(12) United States Patent
Lu et al.

(10) Patent No.: US 11,712,168 B2
(45) Date of Patent: *Aug. 1, 2023

(54) SYSTEM AND METHOD FOR PHYSIOLOGICAL FEATURE DERIVATION

(71) Applicant: VITA-COURSE TECHNOLOGIES (HAINAN) CO., LTD., Hainan (CN)

(72) Inventors: Ying Lu, City of New York, NY (US); Chuanmin Wei, Shenzhen (CN); Heng Peng, Hongkong (CN); Jiwei Zhao, Shenzhen (CN); Ziming Deng, Shenzhen (CN); Zijian Huang, Shenzhen (CN)

(73) Assignee: Vita-Course Technoloaies (Hainan) Co., Ltd., Haikou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/456,644

(22) Filed: Nov. 29, 2021

(65) Prior Publication Data
US 2022/0079459 A1   Mar. 17, 2022

Related U.S. Application Data

(63) Continuation of application No. 16/089,362, filed as application No. PCT/CN2017/076702 on Mar. 15, 2017, now Pat. No. 11,185,242.

(30) Foreign Application Priority Data

Mar. 28, 2016   (WO) ................ PCT/CN2016/077469

(51) Int. Cl.
*A61B 5/02* (2006.01)
*A61B 5/024* (2006.01)
(Continued)

(52) U.S. Cl.
CPC ........ *A61B 5/02416* (2013.01); *A61B 5/0225* (2013.01); *A61B 5/0245* (2013.01);
(Continued)

(58) Field of Classification Search
None
See application file for complete search history.

(56) References Cited

U.S. PATENT DOCUMENTS 5,626,135 A   5/1997 Sanfilippo
5,873,834 A   2/1999 Yanagi et al.
(Continued)

FOREIGN PATENT DOCUMENTS

CN   1698535 A   11/2005
CN   1849998 A   10/2006
(Continued)

OTHER PUBLICATIONS

International Search Report in PCT/CN2017/076702 dated Jun. 7, 2017, 5 pages.
(Continued)

*Primary Examiner* — Ankit D Tejani
(74) *Attorney, Agent, or Firm* — Bay State IP, LLC

(57) ABSTRACT

The present disclosure relates to a device, method and system for calculating, estimating, or monitoring the blood pressure of a subject based on physiological features and personalized models. At least one processor, when executing instructions, may perform one or more of the following operations. A first signal representing a pulse wave relating to heart activity of a subject may be received. A plurality of second signals representing time-varying information on a pulse wave of the subject may be received. A personalized model for the subject may be designated. Effective physiological features of the subject based on the plurality of second signals may be determined. A blood pressure of the (Continued)

subject based on the effective physiological features and the designated model for the subject may be calculated.

18 Claims, 10 Drawing Sheets

(51) Int. Cl.
| | |
|---|---|
| *A61B 5/00* | (2006.01) |
| *A61B 5/021* | (2006.01) |
| *A61B 5/318* | (2021.01) |
| *A61B 5/0225* | (2006.01) |
| *A61B 5/0245* | (2006.01) |
| *A61B 5/11* | (2006.01) |
| *A61B 5/145* | (2006.01) |
| *A61B 5/1455* | (2006.01) |
| *G06F 21/31* | (2013.01) |
| *A61B 5/352* | (2021.01) |
| *A61B 5/026* | (2006.01) |
| *A61B 5/0205* | (2006.01) |
| *A61B 5/01* | (2006.01) |

(52) U.S. Cl.
CPC ...... *A61B 5/02125* (2013.01); *A61B 5/02141* (2013.01); *A61B 5/02255* (2013.01); *A61B 5/1102* (2013.01); *A61B 5/14542* (2013.01); *A61B 5/14551* (2013.01); *A61B 5/318* (2021.01); *A61B 5/7203* (2013.01); *A61B 5/7235* (2013.01); *A61B 5/746* (2013.01); *G06F 21/31* (2013.01); *A61B 5/01* (2013.01); *A61B 5/021* (2013.01); *A61B 5/0205* (2013.01); *A61B 5/026* (2013.01); *A61B 5/352* (2021.01); *A61B 2560/0228* (2013.01)

(56) References Cited

U.S. PATENT DOCUMENTS

| | | |
|---|---|---|
| 6,355,000 B1 | 3/2002 | Ogura |
| 7,674,231 B2 | 3/2010 | McCombie et al. |
| 7,887,491 B2 | 2/2011 | Marks et al. |
| 8,313,439 B2 | 11/2012 | McCombie et al. |
| 9,439,599 B2 | 9/2016 | Thompson et al. |
| 9,865,176 B2 | 1/2018 | Tran |
| 11,185,242 B2* | 11/2021 | Lu .................. A61B 5/1102 |
| 2002/0147402 A1 | 10/2002 | Nitzan et al. |
| 2003/0167012 A1 | 9/2003 | Friedman et al. |
| 2005/0208969 A1 | 9/2005 | Kwoen |
| 2005/0261593 A1 | 11/2005 | Zhang et al. |
| 2007/0100247 A1 | 5/2007 | Platt et al. |
| 2008/0039731 A1 | 2/2008 | McCombie et al. |
| 2008/0221461 A1 | 9/2008 | Zhou et al. |
| 2009/0018422 A1 | 1/2009 | Banet et al. |
| 2009/0105605 A1 | 4/2009 | Abreu |
| 2010/0049006 A1 | 2/2010 | Magar et al. |
| 2010/0087743 A1 | 4/2010 | Hatib et al. |
| 2010/0160798 A1 | 6/2010 | Banet et al. |
| 2011/0009718 A1 | 1/2011 | Gavish |
| 2011/0066045 A1 | 3/2011 | Moon et al. |
| 2011/0231152 A1 | 9/2011 | Kawabe |
| 2012/0101350 A1 | 4/2012 | Bychkov |
| 2012/0136261 A1 | 5/2012 | Sethi et al. |
| 2012/0316448 A1 | 12/2012 | Gu et al. |
| 2013/0012823 A1 | 1/2013 | Ripoll et al. |
| 2013/0053655 A1 | 2/2013 | Castellanos |
| 2013/0197369 A1 | 8/2013 | Xiang |
| 2014/0066788 A1* | 3/2014 | Mukkamala ....... A61B 5/02125 600/485 |
| 2014/0206976 A1 | 7/2014 | Thompson et al. |
| 2015/0018637 A1 | 1/2015 | Chen et al. |
| 2015/0125832 A1 | 5/2015 | Tran |
| 2015/0313486 A1 | 11/2015 | Mestha et al. |
| 2015/0320359 A1 | 11/2015 | Luo |
| 2015/0374244 A1 | 12/2015 | Yoo et al. |
| 2015/0377909 A1 | 12/2015 | Cavet et al. |
| 2016/0270708 A1 | 9/2016 | Tateda et al. |
| 2017/0109495 A1 | 4/2017 | Xin |
| 2018/0116597 A1 | 5/2018 | Yu et al. |
| 2018/0132744 A1 | 5/2018 | Yu et al. |
| 2018/0160905 A1 | 6/2018 | Wang et al. |

FOREIGN PATENT DOCUMENTS

| | | |
|---|---|---|
| CN | 101327121 A | 12/2008 |
| CN | 101732040 A | 6/2010 |
| CN | 101810470 A | 8/2010 |
| CN | 102008296 A | 4/2011 |
| CN | 102397064 A | 4/2012 |
| CN | 102429649 A | 5/2012 |
| CN | 102488503 A | 6/2012 |
| CN | 202505340 U | 10/2012 |
| CN | 103190891 A | 7/2013 |
| CN | 103385702 A | 11/2013 |
| CN | 103598876 A | 2/2014 |
| CN | 103637787 A | 3/2014 |
| CN | 103637788 A | 3/2014 |
| CN | 104173036 A | 12/2014 |
| CN | 204044771 U | 12/2014 |
| CN | 104257371 A | 1/2015 |
| CN | 104323764 A | 2/2015 |
| CN | 104382571 A | 3/2015 |
| CN | 104414626 A | 3/2015 |
| CN | 204207743 U | 3/2015 |
| CN | 104523252 A | 4/2015 |
| CN | 104665768 A | 6/2015 |
| CN | 104706348 A | 6/2015 |
| CN | 104720773 A | 6/2015 |
| CN | 204499693 U | 7/2015 |
| CN | 204506976 U | 7/2015 |
| CN | 104814729 A | 8/2015 |
| CN | 204674751 U | 9/2015 |
| WO | 2007110158 A1 | 10/2007 |
| WO | 2010135516 A2 | 11/2010 |
| WO | 2011008383 A1 | 1/2011 |
| WO | 2012040931 A1 | 4/2012 |
| WO | 2012128407 A1 | 9/2012 |
| WO | 2013171599 A1 | 11/2013 |
| WO | 2014195578 A1 | 12/2014 |
| WO | 2016155138 A1 | 10/2016 |
| WO | 2016155348 A1 | 10/2016 |
| WO | 2017005016 A1 | 1/2017 |

OTHER PUBLICATIONS

Written Opinion in PCT/CN2017/076702 dated Jun. 7, 2017, 5 pages.
International Search Report in PCT/CN2016/077469 dated Jun. 8, 2016, 5 pages.
Written Opinion in PCT/CN2016/077469 dated Jun. 8, 2016, 4 pages.
International Search Report in PCT/CN2015/083334 dated Dec. 18, 2015, 7 pages.
Written Opinion in PCT/CN2015/083334 dated Dec. 18, 2015, 6 pages.
International Search Report in PCT/CN2015/096498 dated Mar. 9, 2016, 7 pages.
Written Opinion in PCT/CN2015/096498 dated Mar. 9, 2016, 5 pages.
International Search Report in PCT/CN2016/070017 dated Apr. 13, 2016, 6 pages.
Written Opinion in PCT/CN2016/070017 dated Apr. 13, 2016, 8 pages.
The Second Office Action in Chinese Application No. 201580078735.9 dated Mar. 16, 2020, 25 pages.

* cited by examiner

SYSTEM AND METHOD FOR PHYSIOLOGICAL FEATURE DERIVATION

CROSS-REFERENCE TO RELATED APPLICATIONS

The application is a Continuation of U.S. application Ser. No. 16/089,362, filed on Sep. 27, 2018, which is a U.S. national stage under 35 U.S.C. § 371 of International Application No. PCT/CN2017/076702, filed on Mar. 15, 2017, which claims priority to International Application No. PCT/CN2016/077469 filed Mar. 28, 2016, each of which is hereby incorporated by reference.

TECHNICAL FIELD

The present disclosure generally relates to a personalized system and method applicable in health-care related areas. More particularly, the present disclosure relates to a system and method for physiological feature derivation and blood pressure monitoring.

BACKGROUND

A traditional blood pressure measurement system, also called sphygmomanometers, employs Korotkoff sounds or an oscillometric method to determine blood pressure based on the relationship of the external pressure and magnitude of arterial volume pulsations. In recent years techniques have been developed using pulse wave signals, obtained from photoelectric sensors placed on the finger of a subject, to derive physiological features and estimate blood pressure. A system utilizing such techniques can be portable and monitor the blood pressure of a subject continuously. Continuous monitoring of multiple physiological features may be beneficial for, for example, hypertension management and cardiovascular risk prediction.

SUMMARY

In a first aspect of the present disclosure, a device is provided. The device includes memory storing instructions and at least one processor that executes the instructions to perform operations comprising: receiving a first signal representing a pulse wave relating to heart activity of a subject; receiving a plurality of second signals representing time-varying information on a pulse wave of the subject; designating a personalized model for the subject; determining effective physiological features of the subject based on the plurality of second signals; and calculating a blood pressure of the subject based on the effective physiological features and the designated model for the subject.

In the device provided above, the receiving the plurality of second signals comprises communicating with one or more second sensors.

Further, in the device provided above, the first sensor comprises a plurality of electrodes, and one of the one or more second sensors comprises a photoelectric sensor.

Further, in the device provided above, the first signal or the second signal comprises an optical signal or an electric signal.

Further, in the device provided above, the effective physiological features are obtained based on Akaike information criterion (AIC).

Further, in the device provided above, the first signal or the second signal comprises an ECG waveform, a PPG waveform, or a BCG waveform.

Further, the device provided above further comprises or is configured to communicate with a cuff-based blood pressure monitor.

Further, in the device provided above, the cuff-based blood pressure monitor being configured to coordinate a blood pressure measurement with the receiving of the first signal or the receiving of the plurality of second signals.

In a second aspect of the present disclosure, a method is provided. The method includes: receiving a first signal representing a pulse wave relating to heart activity of a subject; receiving a plurality of second signals representing time-varying information on a pulse wave of the subject; designating a personalized model for the subject; determining effective physiological features of the subject based on the plurality of second signals; and calculating a blood pressure of the subject based on the effective physiological features and the designated model for the subject.

Further, the method provided above further comprises acquiring the first signal at a first location on the body of the subject.

Further, the method provided above further comprises acquiring the second signal at a second location on the body of the subject.

Further, in the method provided above, the first signal or at least one of the plurality of second signals comprises an optical signal or an electric signal.

Further, in the method provided above, the effective physiological features are obtained based on Akaike information criterion (AIC).

Further, in the method provided above, the first signal or the second signal is acquired in real time or at a first time interval.

Further, in the method provided above, the set of calibration data is acquired at a second time interval.

In a third aspect of the present disclosure, a system is provided. The system includes a first acquisition module configured to receive a first signal representing heart activity of a subject; a second acquisition module configured to receive a plurality of second signals representing time-varying information on the pulse wave; a calibration unit configured to acquire a set of calibration data; an analysis module configured to designate a personalized model for the subject, determine effective physiological features of the subject based on the plurality of second signals, and calculate a blood pressure of the subject based on the effective physiological features and the designated model for the subject.

Further, in the system provided above, the first acquisition module comprises an ECG monitor.

Further, in the system provided above, the second acquisition module comprises a blood oxygen monitor.

Further, in the system provided above, the first signal or one of the plurality of second signals comprises an optical signal or an electric signal.

Further, in the system provided above, the calibration unit comprises or is configured to communicate with a cuff-based blood pressure monitor.

Further, in the system provided above, the cuff-based blood pressure monitor is configured to coordinate a blood pressure measurement with the first signal or the plurality of second signals.

Further, the system provided above further comprises an output module configured to provide the calculated blood pressure for output.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
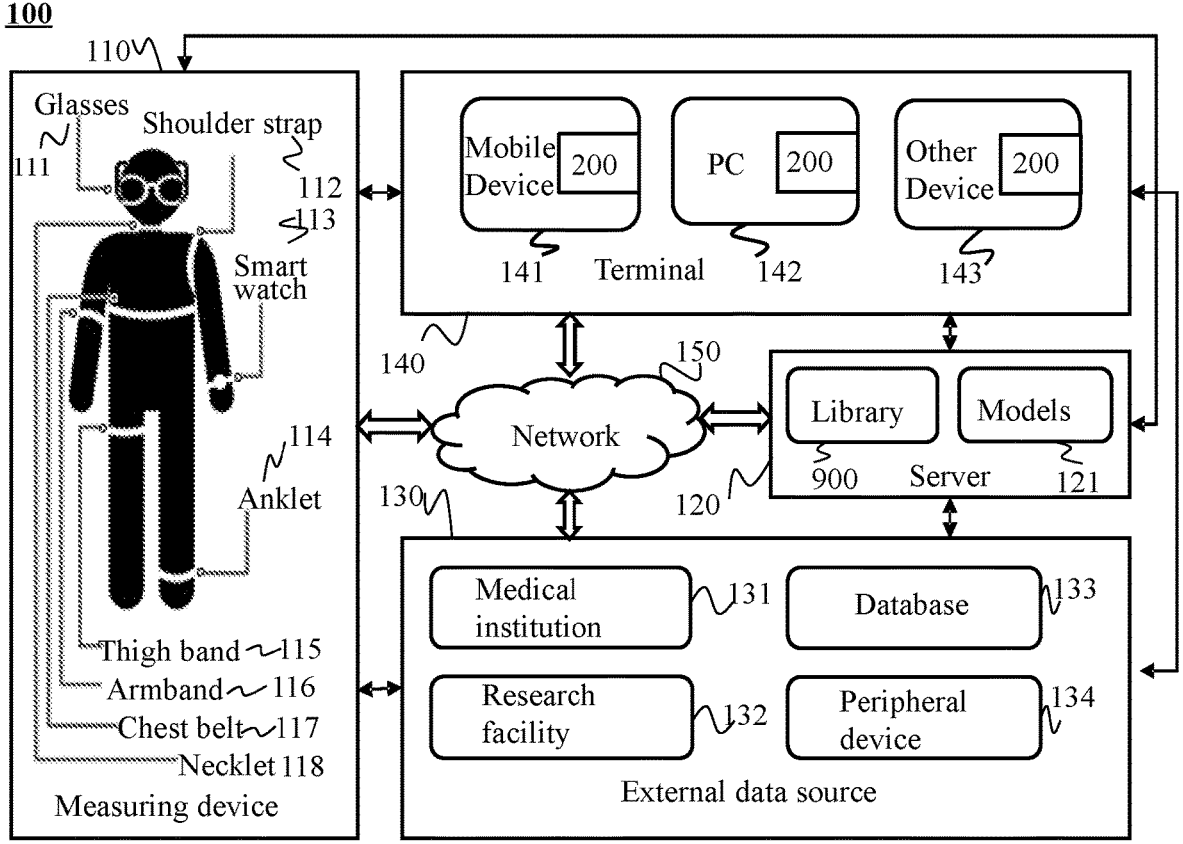
FIG. 1 illustrates an exemplary system configuration in which a system for monitoring a physiological signal may be deployed in accordance with various embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure.

The present disclosure relates to system, method, and programming aspects of physiological feature derivation, for example, blood pressure monitoring. The system and method involve improved signal processing and model monitoring. The system and method as disclosed herein may monitor multiple physiological features. The characteristics of the system and method may include, for example, real time, simultaneity, continuity, non-invasiveness, improved accuracy, or the like, or a combination thereof. In some embodiments, the system and method as disclosed herein may monitor various cardiovascular activities and related information including, for example, blood pressure information, electrocardiography (ECG) information, blood oxygenation information, or the like, or a combination thereof. In some embodiments, a blood pressure may be estimated based on pulse wave related information, for example, pulse transit time (PTT), pulse arrival time (PAT), Fourier spectrum of the pulse wave, wavelet decomposition of the pulse wave, first order derivative and higher order derivatives of the pulse wave, or the like, or a combination thereof. In some embodiments, a blood pressure and/or blood oxygen level may be estimated based on photoplethysmogram (PPG) signals. The system and method as disclosed herein may be used in a healthcare institute (e.g., a hospital) or at home. The following description is provided with reference to the derivation and reduction of physiological features in connection with the blood pressure monitoring for illustration purposes, and is not intended to limit the scope of the present disclosure. Merely by way of example, the system and method as disclosed herein may utilize one or more other pulse wave related processing, for example, artificial intelligence, big data based neural networks, and the like, for blood pressure monitoring.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purposes of illustration and description only and are not intended to limit the scope of the present disclosure. As used in the specification and in the claims, the singular form of "a," "an," and "the" include plural referents unless the context clearly dictates otherwise.

FIG. 1 illustrates an exemplary system configuration in which a system 100 may be deployed in accordance with some embodiments of the present disclosure. The system 100 may monitor one or more physiological pulse wave signals of interest. The system 100 may include a measuring device 110, a server 120, an external data source 70, and a terminal 140. Various components of the system 100 may be connected to each other directly or indirectly via a network 150.

The measuring device 110 may measure a signal. The signal may be a cardiovascular signal. The signal may relate to or be used to calculate or estimate physiological features of interest. In some embodiments, the signal may be a photoplethysmogram (PPG) signal. The physiological features may be one or more spatial, temporal, spectral, and/or personal quantities associated with the PPG signal. For example, the physiological features may include pulse transit time (PTT). The measuring device 110 may include, for example, a clinical device, a household device, a portable device, a wearable device, or the like, or a combination thereof. As used herein, a clinical device may be one that meets applicable standards and/or specifications to be used in a clinical setting including, for example, a hospital, a doctor's office, a nursing home, or the like. A clinical device may be used by or with the assistance of a healthcare provider. As used herein, a household device may be one that meets applicable standards and/or specifications to be used at home or a nonclinical setting. A household device may be used by someone who is or is not a professional provider. A clinical device or a household device, or a portion thereof, may be portable or wearable. Exemplary clinical devices include an auscultatory device, an oscillometric device, an ECG monitor, a PPG monitor, or the like, or a combination thereof. Exemplary household devices include an oscillometric device, a household ECG monitor, a sphygmometer, or the like, or a combination thereof. Exemplary portal devices include an oscillometric device, a portable ECG monitor, a portable PPG monitor, or the like, or a combination thereof. Exemplary wearable devices include a pair of glasses 111, a shoulder strap 112, a smart watch 17, an anklet 114, a thigh band 115, an armband 116, a chest belt 117, a necklet 118, a finger clip (not shown), or the like, or a combination thereof. The above mentioned examples of measuring devices 110 are provided for illustration purposes, and not intended to limit the scope of the present disclosure. A measuring device 110 may be in another form including, for example, a fingerstall, a wristband, a brassiere, an underwear, a chest band, or the like, or a combination thereof.

Merely by way of example, the measuring device 110 is a wearable or portable device that may measure one or more cardiovascular signals. In some embodiments, the wearable or portable device may process at least some of the measured signals, estimate a physiological feature of interest based on the measured signals, display a result including the physiological feature of interest in the form of, for example, an image, an audio alert, perform wired or wireless communication with another device or server (for example, the server 120), or the like, or a combination thereof. In some embodiments, the wearable or portable device may communicate with another device (for example, the terminal 140) or a server (for example, a cloud server). The device or server may process at least some of the measured signals, estimate a physiological feature of interest based on the measured signals, display a result including the physiological feature of interest in the form of, for example, an image, an audio alert, or the like, or a combination thereof.

In some embodiments, the operations of processing the measured signals, estimating a physiological feature, displaying a result, or performing wired or wireless communication may be performed by an integrated device or by separate devices connected to or communicating with each other. Such an integrated device may be portable or wearable. In some embodiments, at least some of the separate devices may be portable or wearable, or located in the vicinity of a subject whose signal is measured or a physiological feature of interest is estimated or monitored. As used herein, a subject may refer to a person or animal whose signal or information is acquired and whose physiological feature is acquired, estimated, or monitored. Merely by way of example, a subject may be a patient whose cardiovascular signals are acquired, and blood pressure estimated or monitored based on the acquired cardiovascular signals. Merely by way of example, the subject wears the measuring device 110 that may measure one or more cardiovascular signals; the measured one or more cardiovascular signals are transmitted to a smart phone that may calculate or estimate one or more physiological features of interest based on the measured signals. The calculated one or more physiological features related to the subject may be input a personalized model for the subject, and the blood pressure of the subject may be calculated based on the one or more physiological features and the personalized model for the subject. In some embodiments, at least some of the separate devices are located in a location remote from the subject. Merely by way of example, the subject wears the measuring device 110 that may measure one or more signals; the measured one or more signals are transmitted to a processor that may calculate or estimate multiple physiological features of interest based on the measured signals; the calculated or estimated physiological features of interest may be provided to the subject, or a user other than the subject (for example, a doctor, a care provider, a family member relating to the subject, or the like, or a combination thereof).

In some embodiments, the measuring devices 110 may include various types of sensors including, for example, an electrode sensor, an optical sensor, a photoelectric sensor, a pressure sensor, an accelerometer, a gravity sensor, a temperature sensor, a moisture sensor, or the like, or a combination thereof. The measuring device may monitor and/or detect one or more types of variables related to the subject including, for example, weight, temperature, humidity, user or subject input, or the like, or a combination thereof. The measuring devices 110 may also include a positioning system, for example, a GPS receiver, or a location sensor, and the position information may be transmitted to the server 120, the external data source 70, the terminal 140, or the like, or a combination thereof, through the network 150. The position information and measured signals may be transmitted simultaneously or successively.

The system may include or communicate with a server configured for storing a library 900 and/or models 121. The server may be the server 120. The server 120 may be a cloud server. Merely by way of example, the server 120 may be implemented in a cloud server that may provide storage capacity, computation capacity, or the like, or a combination thereof. The library 900 may collect or store personal data. The personal data may include static data, dynamic data, or both. Exemplary static data may include various information regarding a subject including identity, contact information, birthday, a health history (for example, whether a subject has a history of smoking, information regarding a prior surgery, a food allergy, a drug allergy, a medical treatment history, a history of genetic disease, a family health history, or the like, or a combination thereof), the gender, the nationality, the height, the weight, the occupation, a habit (for example, a health-related habit such as an exercise habit), the education background, a hobby, the marital status, religious belief, or the like, or a combination thereof. Exemplary dynamic data may include a current health condition of a subject, medications the subject is taking, a medical treatment the subject is undertaking, diet, or the like, or a combination thereof. The library 900 may also include personal calibration data regarding a subject. For example, caliphysiological signals or features (for example, pulse transit time (PTT), systolic blood pressure (SBP), diastolic blood pressure (DBP), or the like) relating to the subject for multiple time points or over a period of time, or the like, or a combination thereof.

The library 900 may be stored locally on a measuring device 110, or a terminal 140. The library 900 may include different sections (e.g., a personal data, a universal data, or the like) with different access control level. For example, personal data may record data and information associated with each individual users, but a subject may have different access permits to different parts of personal data. For example, Subject 1's personal data, Subject 2's personal data, and Subject N's personal data may be stored in the library 900, but Subject 1 may only have full access to his/her personal data and limited access to other user's personal data.

The personal data may further include, but not limited to, headers, histories, and preferences. Additionally, a header may have a subject's basic information and medical records. A header may include, but not limited to, subject's age, gender, race, occupation, health condition, medical history, life style, marital status, and other personal information. A history may record measured data (M), calibration values (C) (or calibration data), results (SBP, DBP, BP) and additional information associated with previous measurement and/or calibration. Furthermore, additional information may be any internal or external variables occurred when a subject is conducting a measurement and/or calibration. External variables may include, room temperature, humidity, air pressure, weather, climate, time, and date, etc. Internal variables such as, body temperature, metabolism rate, mood, level of activity, type of activity, diet, and health condition, etc. The above mentioned examples of additional information are only to provide a better illustration, additional information associated with each measurement and/or calibration may be other types of information, such as viscosity and other rheological data of a subject's blood. In some embodiments, the concepts of additional information and information recorded in a header are interchangeable. When some information originally recorded in a header changes with each measurements, it may also be considered as additional information.

Preference may have information associated with models, for example, a subject's favorite models and coefficients, and favorite models applicability, indicating which favorite model(s) are used under what kind of conditions or with what additional information. A subject's historical data may refer to all the information stored under a history. Preference may also include a rating of a subject, which rates the reliability of the subject's personal data and may be considered as a weight factor when sorting the subject's personal data into peer data. For example, a subject who uploads calibration values (C) every week may have a better rating as compared to another subject who only calibrates once every year. The above mentioned examples of information recorded in a preference, and a preference may include other information, such as which part of personal data a subject is willing to share with other users or organizations.

The universal data may include some non-private or non-personalized data, which may be accessed by other users or subjects. The universal data may include the records of the database of all the models, logics, and public data, for example, models and coefficients, logical judgments to sort peer data from personal data, and statistical results related to calibration values. Peer data may be sorted from multiple subjects' personal data, and logical judgments to sort peer data from personal data serve to find most closely related data according the subjects' headers, and additional information in histories. Logical judgments to sort peer data from personal data may also consider ratings in preferences to weigh the data acquired from different subjects. The above mentioned examples of information recorded in the universal data are only to provide a better illustration, and the universal data may also include other information such as errors (E, E', E") associated with each regression analysis. More description may be found in, for example, International Application No. PCT/CN2015/083334 filed Jul. 3, 2015 and International Application No. PCT/CN2015/096498 filed Dec. 5, 2015, which are hereby incorporated by reference.

One or more models 121 in the server 120 may be applied in data processing or analysis, as described elsewhere in the present disclosure. The description of the server 120 above is provided for illustration purposes, and not intended to limit the scope of the present disclosure. The server 120 may have a different structure or configuration. For example, models 121 are not stored in the server 120; instead, the models 121 may be stored locally at the terminal 140. Furthermore, a library 900 may also be stored at the terminal 140.

The external data sources 70 may include a variety of organizations, systems, and devices, or the like, or a combination thereof. Exemplary data sources 70 may include a medical institution 71, a research facility 72, a database 73, and a peripheral device 74, or the like, or a combination thereof. The medical institution 71 or the research facility 72 may provide, for example, personal medical records, clinical test results, experimental research results, theoretical or mathematical research results, models suitable for processing data, or the like, or a combination thereof. The database 73 may store various data related to a subject, such as physiological features and personal data related to the subject. A peripheral device 74 may monitor and/or detect one or more types of variables including, for example, temperature, humidity, user or subject input, or the like, or a combination thereof. The above mentioned examples of the external data sources 70 and data types are provided for illustration purposes, and not intended to limit the scope of the present disclosure. For instance, the external data sources 70 may include other sources and other types of data, such as genetic information relating to a subject or his family.

The terminal 140 in the system 100 may be configured for processing at least some of the measured signals, estimating a physiological feature of interest based on the measured cardiovascular signals, displaying a result including the physiological feature of interest in the form of, for example, an image, storing data, controlling access to the system 100 or a portion thereof (for example, access to the personal data stored in the system 100 or accessible from the system 100), managing input-output from or relating to a subject, or the like, or a combination thereof. The terminal 140 may include, for example, a mobile device 141 (for example, a smart phone, a tablet, a laptop computer, or the like), a personal computer 142, other devices 143, or the like, or a combination thereof. Other devices 143 may include a device that may work independently, or a processing unit or processing module assembled in another device (for example, an intelligent home terminal). Merely by way of example, the terminal 140 includes a CPU or a processor in a measuring device 110. In some embodiments, the terminal 140 may include an engine 200 as described in FIG. 2, and the terminal 140 may also include a measuring device 110.

The network 150 may be a single network or a combination of different networks. For example, the network 150 may be a local area network (LAN), a wide area network (WAN), a public network, a private network, a proprietary network, a Public Telephone Switched Network (PSTN), the Internet, a wireless network, a virtual network, or any combination thereof. The network 150 may also include various network access points, for example, wired or wireless access points such as base stations or Internet exchange points (not shown in FIG. 1), through which a data source or any component of the system 100 described above may connect to the network 150 in order to transmit information via the network 150.

Various components of or accessible from the system 100 may include a memory or electronic storage media. Such components may include, for example, the measuring device 110, the server 120, the external data sources 70, the terminal 140, peripheral device 74 discussed in connection with FIG. 2, or the like, or a combination thereof. The memory or electronic storage media of any component of the system 100 may include one or both of a system storage (for example, a disk) that is provided integrally (i.e. substantially non-removable) with the component, and a removable storage that may be removably connected to the component via, for example, a port (for example, a USB port, a firewire port, etc.) or a drive (for example, a disk drive, etc.). The memory or electronic storage media of any component of the system 100 may include or be connectively operational with one or more virtual storage resources (for example, cloud storage, a virtual private network, and/or other virtual storage resources).

The memory or electronic storage media of the system 100 may include a dynamic storage device that may store information and instructions to be executed by the processor of a system-on-chip (SoC, for example, a chipset including a processor), other processors (or computing units), or the like, or a combination thereof. The memory or electronic storage media may also be used to store temporary variables or other intermediate information during execution of instructions by the processor(s). Part of or the entire memory or electronic storage media may be implemented as Dual In-line Memory Modules (DIMMs), and may be one or more of the following types of memory: static random access memory (SRAM), Burst SRAM or Synch Burst SRAM (BSRAM), dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), Sync Link DRAM (SLDRAM), Direct Rambus DRAM (DRDRAM), Ferroelectric RAM (FRAM), or any other type of memory device. The memory or electronic storage media may also include read-only memory (ROM) and/or another static storage device that may store static information and instructions for the processor of the SoC and/or other processors (or computing units). Further, the memory or electronic storage media may include a magnetic disk, optical disc or flash memory devices to store information and instructions.

In some embodiments, the SoC may be part of a core processing or computing unit of a component of or accessible from the system 100. The SoC may receive and process input data and instructions, provide output and/or control other components of the system. In some embodiments, the SoC may include a microprocessor, a memory controller, a memory, and a peripheral component. The microprocessor may further include a cache memory (for example, SRAM), which along with the memory of the SoC may be part of a memory hierarchy to store instructions and data. The microprocessor may also include one or more logic modules such as a field programmable gate array (FPGA) or other logic array. Communication between the microprocessor in the SoC and memory may be facilitated by the memory controller (or chipset), which may also facilitate in communicating with the peripheral component, such as a counter-timer, a real-time timer, a power-on reset generator, or the like, or a combination thereof. The SoC may also include other components including, for example, a timing source (for example, an oscillator, a phase-locked loop, or the like), a voltage regulator, a power management circuit, or the like, or a combination thereof.

Merely by way of example, the system 100 may include a wearable or portable device. The wearable or portable device may include a SoC and a plurality of sensors. Exemplary sensors may include a photoelectric sensor, a conductance sensor, or the like, or a combination thereof. The SoC may process signals acquired through at least some of the plurality of sensors. The acquired signals may be various physiological signals including, for example, photoplethysmograph (PPG), electrocardiograph (ECG), or the like, or a combination thereof. The SoC may calculate a physiological feature of interest based on the acquired signals. Exemplary physiological features of interest may be blood pressure, blood oxygen level, ECG information, heart rate, or the like, or a combination thereof.

In some embodiments, the external data source 70 may receive data from the measuring device 110, the sever 120, the terminal 140, or the like, or any combination by the network 150. Merely by way of example, the external data source 70 (for example, a medical institution, or a smart home system, or the like) may receive information relating to a subject (for example, location information, data from the cloud sever or a terminal, or the like, or a combination thereof) based on the data received from the measuring devices 110 or the terminals 140. In some embodiments, the measuring device 110 may receive data from the sever 120, the external data source 70, or the like, or any combination, via the network 150. Merely by way of example, the measuring device 110 may receive the information relating to a subject (for example, a current/historical health condition of a subject, medications the subject is taking, medical treatment the subject is undertaking, current/historical diets, current emotion status, historical physiological features (for example, PTT, SBP, DBP) relating to the subject, or the like, or a combination thereof). Furthermore, the terminal 140 may receive data from the measuring device 110, the server 120, the external data source 70, or the like, or a combination thereof.

FIG. 1 is a specific example of the system 100, and the configuration of the system 100 is not limited to that illustrated in FIG. 1. For example, a server 120 may be omitted, migrating all of its functions to a terminal 140. In another example, a server 120 and a terminal 140 may both be omitted, migrating all of their functions to a measuring device 110. The system may include various devices or combinations of devices in different embodiments.

In an example, the system may include a wearable or portable device and a mobile device (for example, a smart phone, a tablet, a laptop computer, or the like). The wearable or portable device may be used to acquire physiological signals, environmental information, or the like, or a combination thereof. The mobile device may be used to receive the signals or information acquired by the wearable or portable device. The mobile device may calculate one or more physiological features of interest based on the acquired signals or information, as well as relevant data retrieved from another source (for example, from a server, a memory incorporated in the wearable or portable device, a memory incorporated in the mobile device, etc.). The retrieved relevant data may include, for example, current/historical information stored on the server. Exemplary current/historical information may include a current/historical health condition of a subject, current/historical medications the subject is/was taking, current/historical medical treatment the subject is/was undertaking, current/historical diets, current/historical emotion status, current/historical physiological features (for example, PTT, SBP, DBP, ECG information, heart rate, blood oxygen level) relating to the subject, or the like, or a combination thereof. The wearable or portable device, or the mobile device may display or report, or store at least some of the acquired signals, information, the retrieved relevant data, the calculated one or more physiological features of interest, or the like, or a combination thereof. The display or report may be provided to a subject, a user other than the subject, a third party, the server, or another device.

In another example, the system may include a wearable or portable device that may perform functions including: acquiring physiological signals or environmental information, retrieving relevant data from another source (for example, from a server, a memory incorporated in the wearable or portable device, etc.), calculating one or more physiological features related to a subject based on the acquired signals, information, or the retrieved relevant data, determining a personalized model for the subject, computing the blood pressure of the subject based on the personalized model and the one or more physiological features related to a subject, displaying, reporting, or storing at least some of the acquired signals, information, the retrieved relevant data, the calculated one or more physiological features of interest, the blood pressure of the subject, or the like, or a combination thereof. The display or report may be provided to the subject, a user other than the subject, a third party, the server, or another device.

In a further example, the system may include a wearable or portable device that may perform functions including: acquiring physiological signals related to a subject and environmental information, communicating with a server to transmit at least some of the acquired signals or information to the server such that the server may calculate one or more physiological features of the subject, determining a personalized model for the subject, computing the blood pressure of the subject based on the personalized model and the one or more physiological features related to a subject, receiving the calculated one or more physiological features and/or the blood pressure of the subject from the server, displaying, reporting or storing at least some of the acquired signals, information, the calculated one or more physiological features of interest, the blood pressure of the subject, or the like, or a combination thereof. The display or report may be provided to the subject, a user other than the subject, a third party, the server, or another device. In some embodiments, the communication between the wearable or portable device and the server may be achieved by way of the wearable or portable device being connected to a network (for example, the network 150). In some embodiments, the communication between the wearable or portable device and the server may be achieved via a communication device (for example, a mobile device such as a smart phone, a tablet, a laptop computer, or the like) that communicates with both the wearable or portable device and the server.

In still a further example, the system may include a wearable or portable device, a mobile device (for example, a smart phone, a tablet, a laptop computer, or the like), and a server. The wearable or portable device may be used to acquire physiological signals, environmental information, or the like, or a combination thereof. The mobile device may be used to receive the signals or information acquired by the wearable or portable device, and may calculate one or more physiological features of interest based on the received signals and/or information retrieved from the wearable or portable device, as well as relevant data retrieved from, for example, a server, a memory incorporated in the wearable or portable device or incorporated in the mobile device. The mobile device may display, report, or store at least some of the acquired signals, information, the retrieved relevant data, the calculated one or more physiological features of interest, or the like, or a combination thereof. The display or report may be provided to a subject, a user other than the subject, a third party, the server, or another device.

In still a further example, the system may include an integrated clinical device or a household device. The integrated device may be wearable or portable. The integrated device may be used to acquire physiological signals, environmental information, or the like, or a combination thereof. The integrated device may further include an output device that may display, report, or output at least some of the acquired signals, information, the retrieved relevant data, the calculated one or more physiological features of interest, or the like, or a combination thereof. The display or report may be provided to a subject, a user other than the subject, a third party, the server, or another device. The integrated device may perform one or more measurements for calibrating the integrated device.

In still a further example, the system may include an integrated clinical device or a household device and a server. The integrated device may be wearable or portable. The integrated device may perform functions including: acquiring physiological signals and environmental information, communicating with a server to transmit at least some of the acquired signals or information to the server such that the server may calculate one or more physiological features of interest, receiving the calculated one or more physiological features of interest from the server, displaying, reporting or storing at least some of the acquired signals, information, the calculated one or more physiological features of interest, or the like, or a combination thereof. The display or report may be provided to a subject, a user other than the subject, a third party, the server, or another device. The integrated device may perform one or more measurements for calibrating the integrated device. In some embodiments, the communication between the integrated clinical device or the household device and the server may be achieved by way of the integrated clinical device or the household device being connected to a network (for example, the network 150). In some embodiments, the communication between the integrated device and the server may be achieved via a communication device (for example, a mobile device such as a smart phone, a tablet, a laptop computer, or the like) that communicates with both the wearable or portable device and the server.

In some embodiments, the system may provide a user interface to allow a subject, a user other than the subject, or an entity to exchange information (including input into or output from the system) with the system as disclosed herein. The user interface may be implemented on a terminal device including, for example, a mobile device, a computer, or the like, or a combination thereof. The user interface may be integrated in the system, e.g., a display device of the system. The access to the system may be allowed to one who has an appropriate access privilege. An access privilege may include, for example, a privilege to read some or all information relating to a subject, update some or all information relating to a subject, or the like, or a combination thereof. The access privilege may be associated with or linked to a set of login credentials. Merely by way of example, the system may provide three tiers of access privileges. A first tier may include a full access privilege regarding information relating to a subject, allowing both receiving and updating information relating to a subject. A second tier may include a partial access privilege regarding information relating to a subject, allowing receiving and updating part of information relating to a subject. A third tier may include a minimal access privilege regarding information relating to a subject, allowing receiving or updating part of information relating to a subject Different login credentials may be associated with different access privilege to the information relating to a subject in the system. As used herein, updating may include providing information that does not exist in the system, or modifying pre-existing information with new information.

Merely by way of example, the system may receive information relating to a subject provided via the user interface. The information relating to a subject may include basic information and optional information. Exemplary basic information may include the height, the weight, the age (or the date of birth), the gender, the arm length, the nationality, the occupation, a habit (for example, a health-related habit such as an exercise habit), the education background, a hobby, the marital status, religious belief, a health-related history (for example, whether a subject has a history of smoking, a food allergy, a drug allergy, a medical treatment history, a family health history, a history of genetic disease, information regarding a prior surgery, or the like, or a combination thereof), contact information, emergency contact, or the like, or a combination thereof. Exemplary optional information may include, current health condition of the subject, medications the subject is taking, a medical treatment the subject is undertaking, diet. The system may receive, via the user interface, information relating to a specific measurement of, for example, a physiological feature of interest. Examples of such information may include the motion state of the subject at or around the acquisition time (defined elsewhere in the present disclosure), the emotional state at or around the acquisition time, the stress level at or around the acquisition time, or the like, or a combination thereof. The system may receive, via the user interface, one or more options or instructions. In some embodiments, the options or instructions may be provided by a subject or a user other than the subject answering questions or making selections in response to questions or prompts by the system. In one example, the options or instructions may include a measurement frequency (for example, once a week, once a month, twice a week, twice a month, once a day, twice a day, or the like), a preferred format of the presentation of information to the subject or a user other than the subject (for example, email, a voice message, a text message, an audio alert, haptic feedback, or the like, or a combination thereof). In another example, the options or instructions may include information relating to calculating features of interest, for example, rules regarding how to select a model, a function, calibration data, or the like, or a combination thereof.

In some embodiments, the system may provide, via the user interface, information to a subject, or a user other than the subject. Exemplary information may include an alert, a recommendation, a reminder, or the like, or a combination thereof. In one example, an alert may be provided or displayed to the subject or a user other than the subject if a triggering event occurs. Exemplary triggering events may be that at least some of the acquired information or a physiological feature of interest exceeds a threshold. Merely by way of example, a triggering event may be that the acquired heart rate exceeds a threshold (for example, higher than 150 beats per minute, lower than 40 beats per minute, or the like). As another example, a triggering event may be that the physiological feature of interest, for example, an estimated blood pressure, exceeds a threshold. In another example, a recommendation may be provided or displayed to the subject or a user other than the subject. Exemplary recommendations may be a request to input specific data (for example, basic information, optional information, updated features of interest, updated models, updated functions, updated options and instructions, or the like, or a combination thereof). A reminder may be provided or displayed to the subject or a user other than the subject. Exemplary reminders may include a reminder to take a prescription medication, take a rest, take a measurement of a physiological feature of interest, or the like, or a combination thereof.

In some embodiments, the system may communicate with the subject, a user other than the subject, and/or a third party through the user interface. Exemplary third parties may be a doctor, a healthcare worker, a medical institution, a research facility, a peripheral device of the subject or a user well-connected to the subject, or the like. Exemplary communications may relate to the health conditions of the subject, a dietary habit, an exercise habit, a prescription medication, instructions or steps to conduct a measurement, or the like, or a combination thereof. In some embodiments, a user interface accessible to or by a third party may be the same as, or different from a user interface accessible to or by a subject. In one example, an output or data may be transmitted to a third party (for example, a computer, a terminal at a doctor's office, a hospital where a health care provider is located and the health condition of the subject is being monitored, or the like, or a combination thereof). The third party may provide feedback information or instructions related to the output information via the user interface. Merely by way of example, a third party may receive information regarding one or more physiological features of interest relating to a subject, and accordingly provide a recommendation of actions to be taken by the subject (for example, to take a prescription medication, to take a rest, to contact or visit the third party, or the like, or a combination thereof); the system may relay the recommendation to the subject.

Figure 2:
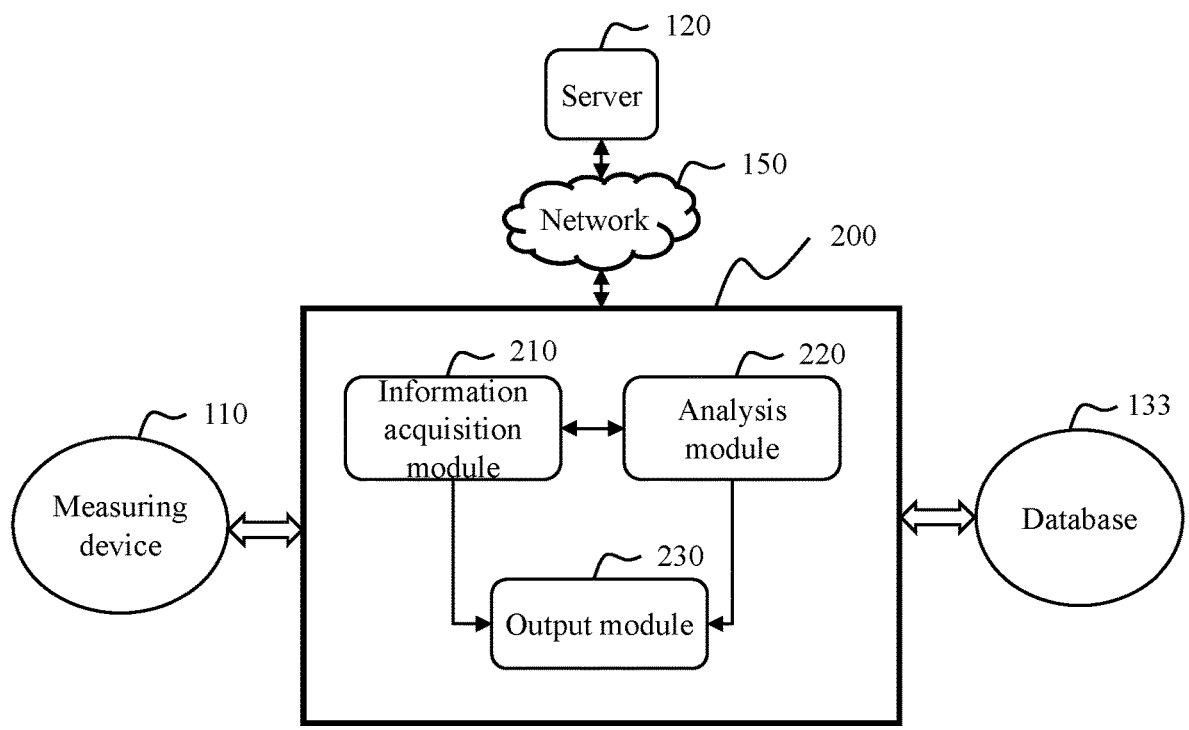
FIG. 2 depicts an exemplary diagram of an engine of the system illustrated in FIG. 1, according to some embodiments of the present disclosure.

FIG. 2 shows an exemplary diagram including the engine 200. The engine 200 may be configured for acquiring one or more signals related to a subject and calculating or estimating blood pressure of the subject based on one or more physiological features derived from the acquired signals. As illustrated, the engine 200 may be connected to or otherwise communicate with, for example, measuring device 110, the database 73, and the server 120. The engine 200 may include an information acquisition module 210, an analysis module 220, and an output module 230. The information acquisition module 210 may be configured for acquiring a signal or information relating to a subject, for example, a physiological signal, information relating to the health condition of the subject, or the like, or a combination thereof. The analysis module 220 may be configured for analyzing the acquired signal or information, or determining or estimating physiological features of interest, or determining a personalized model for a subject, or determining the blood pressure of the subject based on the personalized model. The output module 230 may be configured for outputting the acquired signal or information, the physiological feature of interest, the blood pressure of the subject, or the like, or a combination thereof. As used herein, a module may have an independent processor, or use system shared processor(s). The processor(s) may perform functions according to instructions related to various modules. For example, the analysis module 220, according to relevant instructions, may retrieve acquired signals and perform calculations to obtain one or more physiological feature of interest.

The information acquisition module 210 may be configured for acquiring a signal or information from or relating to one or more subjects. As used herein, acquiring may be achieved by way of receiving a signal or information sensed, detected, or measured by, for example, a sensor, or by way of receiving an input from a subject or from a user other than the subject (for example, a doctor, a care provider, a family member relating to the subject, or the like, or a combination thereof). For brevity, an acquired signal or information may be referred to as acquired information. As used herein, information may include a signal relating to a subject that is acquired by a device including, for example, a sensor, environmental information that is acquired by a device including, for example, a sensor, information that is acquired otherwise including, for example, from an input by a subject or a user other than the subject, a processed or pre-treated information that is acquired as described, or the like, or a combination thereof. Exemplary sensors may include an electrode sensor, an optical sensor, a photoelectric sensor, a pressure sensor, an accelerometer, a gravity sensor, a temperature sensor, a moisture sensor, or the like, or a combination thereof.

Exemplary acquired information may include physiological information. In the exemplary context of determining blood pressure, the physiological information may include a cardiovascular signal. Exemplary cardiovascular signals may include a photoplethysmogram (PPG) signal, an electrocardiogram (ECG) signal, a ballistocardiogram (BCG) signal, a blood pressure (BP), a systolic blood pressure (SBP), a diastolic blood pressure (DBP), a pulse rate (PR), a heart rate (HR), a heart rate variation (HRV), cardiac murmur, blood oxygen saturation, a density of blood, a pH value of the blood, a bowel sound, a brainwave, a fat content, a blood flow rate, or the like, or a combination thereof. Exemplary acquired information may include information regarding a subject, for example, the height, the weight, the age, the gender, the body temperature, the arm length, an illness history, or the like, or a combination thereof. Exemplary acquired information may include information from or relating to the ambient surrounding a subject (referred to as environmental information) at or around the acquisition time. Exemplary environmental information may include temperature, humidity, air pressure, an air flow rate, an ambient light intensity, or the like, or a combination thereof. As used herein, the acquisition time may refer to a time point or a time period when information relating to the subject, for example, physiological information of the subject, is acquired.

The information acquisition module 210 may receive or load information from the measuring device 110, the server 120, the database 73, or other devices (not shown) including, for example, an ECG monitor, a PPG monitor, a respiratory monitor, a brainwave monitor, a blood oxygen monitor, a blood glucose monitor, and a device having similar functions. In the disclosure, the term "monitor" and the term "sensor" may be used interchangeably. Examples of measuring device 110 may include a smart watch, a finger clip, an earphone, a pair of glasses, a bracelet, a necklace, or the like, or a combination thereof. The measuring device 110, the server 120, the database 73, or other devices may be local or remote. For example, the server 120 and the engine 200 may be connected through a local area network (LAN), or Internet. The measuring device 110 and the engine 200 may be connected through a local area network, or Internet. Other devices and the engine 200 may be connected through a local area network, or Internet. The information transmission between the information acquisition module 210 and the measuring device 110, the server 120, the database 73, or such other devices may be via a wired connection, a wireless connection, or the like, or a combination thereof.

The information acquisition module 210 may receive information provided by a subject or a user other than the subject via, for example, an input device. The input device may include but is not limited to a keyboard, a touch screen (for example, with haptics or tactile feedback), a speech input device, an eye tracking input device, a brain monitoring system, or the like, or a combination thereof. The information received through the input device may be transmitted to a processor, via, for example, a bus, for further processing. The processor for further processing the information obtained from the input device may be a digital signal processor (DSP), a SoC (system on the chip), or a microprocessor, or the like, or the combination thereof. Other types of input device may include cursor control device, such as a mouse, trackball, or cursor direction keys to convey information about direction and/or command selections, for example, to the processor.

The description of the information acquisition module 210 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a storage unit (not shown in FIG. 2) may be added to the information acquisition module 210 for storing the acquired information.

The analysis module 220 may be configured for analyzing acquired information. The analysis module 220 may be connected to or otherwise communicate with one or more information acquisition modules 210-1, 210-2, ..., 210-N to receive at least part of the acquired information. The analysis module 220 may be configured for performing one or more operations including, for example, a pre-processing, a calculation, a calibration, a statistical analysis, or the like, or a combination thereof. Any one of the operations may be performed based on at least some of the acquired information, or an intermediate result from another operation (for example, training data, or an operation performed by the analysis module 220, or another component of the system 100). For instance, the analysis may include one or more operations including pre-processing at least part of the acquired information relating to a subject, identifying characteristic points or features of the acquired information or the pre-treated information, determining a personalized model for the subject, calculating the blood pressure of the subject, analyzing the information regarding the subject provided by the subject or a user other than the subject, analyzing the information regarding the ambient environment surrounding the subject at or around the acquisition time, or the like, or a combination thereof.

Some operations of the analysis may be performed in parallel or in series. As used herein, a parallel performance may indicate that some operations of the analysis may be performed at or around the same time; a serial performance may indicate that some operations of the analysis may commence or be performed after other operations of the analysis have commenced or finished. In some embodiments, a serial performance of two operations may indicate that one operation commences after the other operation has finished. In some embodiments, a serial performance of two operations may indicate that one operation commences after the other operation has commenced, and the two operations partially overlap. In some embodiments, at least two operations of an analysis may be performed in parallel. In some embodiments, at least two operations of an analysis may be performed in series. In some embodiments, some of the operations of an analysis may be performed in parallel, and some of the operations may be performed in series.

The analysis, or some operations of the analysis, may be performed in real time, i.e. at or around the acquisition time. The analysis, or some operations of the analysis, may be performed after a delay since the information is acquired. In some embodiments, the acquired information is stored for analysis after a delay. In some embodiments, the acquired information is pre-treated and stored for further analysis after a delay. The delay may be in the order of seconds, or minutes, or hours, or days, or longer. After the delay, the analysis may be triggered by an instruction from a subject or a user other than the subject (for example, a doctor, a care provider, a family member relating to the subject, or the like, or a combination thereof), an instruction stored in the system 100, or the like, or a combination thereof. Merely by way of example, the instruction stored in the system 100 may specify the duration of the delay, the time the analysis is to be performed, the frequency the analysis is to be performed, a triggering event that triggers the performance of the analysis, or the like, or a combination thereof. The instruction stored in the system 100 may be provided by a subject or a user other than the subject. An exemplary triggering event may be that at least some of the acquired information or a physiological feature of interest exceeds a threshold. Merely by way of example, a triggering event may be that the acquired heart rate exceeds a threshold (for example, higher than 150 beats per minute, lower than 40 beats per minute, or the like). As used herein, "exceed" may be larger than or lower than a threshold. As another example, a triggering event may be that the physiological feature of interest, for example, an estimated blood pressure, exceeds a threshold.

The analysis module 220 may be centralized or distributed. A centralized analysis module 220 may include a processor (not shown in FIG. 2). The processor may be configured for performing the operations. A distributed analysis module 220 may include a plurality of operation units (not shown in FIG. 2). The operation units may be configured for collectively performing the operations of a same analysis. In the distributed configuration, the performance of the plurality of operation units may be controlled or coordinated by, for example, the server 120.

The acquired information, an intermediate result of the analysis, or a result of the analysis (for example, a physiological feature of interest) may be analog or digital. In an exemplary context of blood pressure monitoring, the acquired information, an intermediate result of the analysis, or a result of the analysis (for example, a physiological feature of interest) may include, for example, a PPG signal, an ECG signal, a BCG signal, a BP, a SBP, a DBP, a PR, a HR, a HRV (heart rate variation), cardiac murmur, blood oxygen saturation (or referred to as blood oxygen level), a blood density, a pH value of the blood, a bowel sound, a brainwave, a fat content, a blood flow rate, or the like, or a combination thereof.

A result of the analysis, for example, a physiological feature of interest regarding a subject, may be influenced by various factors or conditions including, for example, an environmental factor, a factor due to a physiological condition of a subject, a factor due to a psychological condition of a subject, or the like, or a combination thereof. One or more of such factors may influence the accuracy of the acquired information, the accuracy of an intermediate result of the analysis, the accuracy of a result of the analysis, or the like, or a combination thereof. For instance, a physiological feature of interest may be estimated based on a correlation with the acquired information; a factor due to a physiological condition may cause a deviation from the correlation; the factor may influence the accuracy of the physiological feature of interest that is estimated based on the correlation. Merely by way of example, a cardiovascular signal relating to a subject may vary with, for example, time, the psychological condition of the subject, or the like, or a combination thereof. The correlation between a cardiovascular signal with a physiological feature (for example, the correlation between a PPT value and a blood pressure) of a subject may vary with, for example, the physiological condition of the subject, the psychological condition of the subject, the ambient surrounding the subject, or the like, or a combination thereof. Such an influence may be counterbalanced or compensated in the analysis.

In an analysis, information relating to an influencing condition (for example, environmental information, a physiological condition, a psychological condition, or the like) may be acquired, and a correction or adjustment may be made accordingly in the analysis process. Merely by way of example, the correction or adjustment may be by way of a correction factor. For instance, an environmental correction factor may be introduced into the analysis based on acquired environmental information from or relating to the ambient surrounding a subject at or around the acquisition time. Exemplary environmental information may include one or more of temperature, humidity, air pressure, an air flow rate, an ambient light intensity, or the like. Exemplary environmental correction factors may include one or more of a temperature correction factor, a humidity correction factor, an air pressure correction factor, an air flow rate correction factor, an ambient light intensity correction factor, or the like. As another example, the correction or adjustment may be by way of performing a calibration of the correlation (for example, a calibrated model, a calibrated function, or the like) used to estimate the physiological feature of interest. As a further example, the correction or adjustment may be by way of choosing, based on information relating to an influencing condition, a correlation from a plurality of correlations used to estimate the physiological feature of interest.

This description of the analysis module 220 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a cache unit (not shown in FIG. 2) may be added to the analysis module 220 used for storing an intermediate result or real time signal or information during the processes above mentioned.

The output module 230 may be configured for providing an output. The output may include a physiological feature of interest, at least some of the acquired information (for example, the acquired information that is used in estimating the physiological feature of interest), the blood pressure of a subject, or the like, or a combination thereof. The transmission of the output may be via a wired connection, a wireless connection, or the like, or a combination thereof. The output may be transmitted real-time once the output is available for transmission. The output may be transmitted after a delay since the output is available for transmission. The delay may be in the order of seconds, or minutes, or hours, or days, or longer. After the delay, the output may be triggered by an instruction from a subject, a user other than the subject, or a related third party, an instruction stored in the system 100, or the like, or a combination thereof. Merely by way of example, the instruction stored in the system 100 may specify the duration of the delay, the time the output is to be transmitted, the frequency output is to be transmitted, a triggering event, or the like, or a combination thereof. The instruction stored in the system 100 may be provided by a subject or a user other than the subject. An exemplary triggering event may be that the physiological feature of interest or that at least some of the acquired information exceeds a threshold. Merely by way of example, a triggering event may be that the acquired heart rate exceeds a threshold (for example, higher than 150 beats per minute, lower than 40 beats per minute, or the like). As another example, a triggering event may be that the physiological feature of interest, for example, an estimated blood pressure, exceeds a threshold.

The output for transmission may be of, for example, an analog form, a digital form, or the like, or a combination thereof. The output may be in the format of, for example, a graph, a code, a voice message, text, video, an audio alert, a haptic effect, or the like, or a combination thereof. The output may be displayed on a local terminal, or transmitted to a remote terminal, or both. A terminal may include, for example, a personal computer (PC), a desktop computer, a laptop computer, a smart phone, a smart watch, or the like, or a combination thereof. Merely by way of example, an output may be displayed on a wearable or portable device a subject wears, and also transmitted to a computer or terminal at a doctor's office or a hospital where a health care provider is located and monitors the health condition of the subject.

The output module 230 may include or communicate with a display device that may display output or other information to a subject or a user other than the subject. The display device may include a liquid crystal display (LCD), a light emitting diode (LED)-based display, or any other flat panel display, or may use a cathode ray tube (CRT), a touch screen, or the like. A touch screen may include, for example, a resistance touch screen, a capacity touch screen, a plasma touch screen, a vector pressure sensing touch screen, an infrared touch screen, or the like, or a combination thereof.

In some embodiments, a storage module (not shown in FIG. 2) or a storage unit (not shown in FIG. 2) may be integrated in the engine 200. In some embodiments, a storage unit (not shown in FIG. 2) may be integrated in any one of the information acquisition module 210, the analysis module 220, or the output module 230. The storage module (not shown in FIG. 2) or the storage unit (not shown in FIG. 2) may be used for storing an intermediate result, or a result of an analysis. The storage module (not shown in FIG. 2) or the storage unit (not shown in FIG. 2) may be used as a data cache. The storage module (not shown in FIG. 2) or the storage unit (not shown in FIG. 2) may include a hard disk, a floppy disk, selectron storage, RAM, DRAM, SRAM bubble memory, thin film memory, magnetic plated wire memory, phase change memory, flash memory, cloud disk, or the like, or a combination thereof. The storage module (not shown in FIG. 2) or the storage unit (not shown in FIG. 2) may include memory or electronic storage media described in connection with FIG. 1 and elsewhere in the present disclosure.

In some embodiments, the engine 200 does not include a storage module or a storage unit, and the measuring device 110 or the server 120 may be used as a storage device accessible by the engine 200. The server 120 may be a cloud server providing cloud storage. As used herein, cloud storage is a model of data storage where digital data are stored in logical pools, physical storage spanning multiple servers (and often located at multiple locations). The physical environment including, for example, the logical pools, the physical storage spanning multiple servers may be owned and managed by a hosting company. The hosting company may be responsible for keeping the data available and accessible, and the physical environment protected and running. Such cloud storage may be accessed through a cloud service, a web service application programming interface (API), or by applications that utilize the API. Exemplary applications include cloud desktop storage, a cloud storage gateway, a Web-based content management system, or the like, or a combination thereof. The server 120 may include a public cloud, a personal cloud, or both. For example, the acquired information may be stored in a personal cloud that may be accessed after authorization by way of authenticating, for example, a username, a password, a secret code, or the like, or a combination thereof. Non personalized information including, for example, methods or calculation models, may be stored in a public cloud. No authorization or authentication is needed to access the public cloud. The information acquisition module 210, the analysis module 220 and the output module 230 may retrieve or load information or data from the public cloud or the personal clouds. Any one of these modules may transmit signals and data to the public cloud or personal cloud.

Connection or transmission between any two of the information acquisition module 210, the analysis module 220, and the output module 230 may be via a wired connection, a wireless connection, or the like, or a combination thereof. At least two of these modules may be connected with different peripheral equipment. At least two of these modules may be connected with the same peripheral equipment. The measuring device 110 may be connected with one or more modules via a wired connection, a wireless connection, or the like, or a combination thereof. Those skilled in the art should understand that the above embodiments are only utilized to describe the invention in the present disclosure. There are many modifications and variations to the present disclosure without departing the spirit of the invention disclosed in the present disclosure. For example, the information acquisition module 210 and the output module 230 may be integrated in an independent module configured for acquiring and outputting signals or results. The independent module may be connected with the analysis module 220 via a wired connection, a wireless connection, or the like, or a combination thereof. The three modules in the engine 200 may be partially integrated in one or more independent modules or share one or more units.

The connection or transmission between the modules in the system 100, or between the modules and the measuring device 110, or between the system and the server 120 should not be limited to the descriptions above. All the connections or transmissions may be used in combination or may be used independently. The modules may be integrated in an independent module, i.e. functions of the modules may be implemented by the independent module. Similarly, one or more modules may be integrated on a single piece of measuring device 110. Any one of the connections or transmissions mentioned above may be via a wired connection, a wireless connection, or the like, or a combination thereof. For example, the wired connection or wireless connection may include, for example, a wire, a cable, satellite, microwave, blue tooth, radio, infrared, or the like, or a combination thereof.

The engine 200 may be implemented on one or more processors. The modules or units of the engine 200 may be integrated in one or more processors. For example, the information acquisition module 210, the analysis module 220, and the output module 230 may be implemented on one or more processors. The one or more processors may transmit signals or data with a storage device (not shown in FIG. 2), the peripheral equipment 240, and the server 120. The one or more processors may retrieve or load signals, information, or instructions from the storage device (not shown in FIG. 2), or the server 120, and process the signals, information, data, or instructions, or a combination thereof, to calculate one or more physiological features of interest.

The one or more processors may also be connected or communicate with other devices relating to the system 100, and transmit or share signals, information, instructions, the physiological features of interest, or the like with such other devices via, for example, a mobile phone APP, a local or remote terminal, or the like, or a combination thereof.

Figure 3:
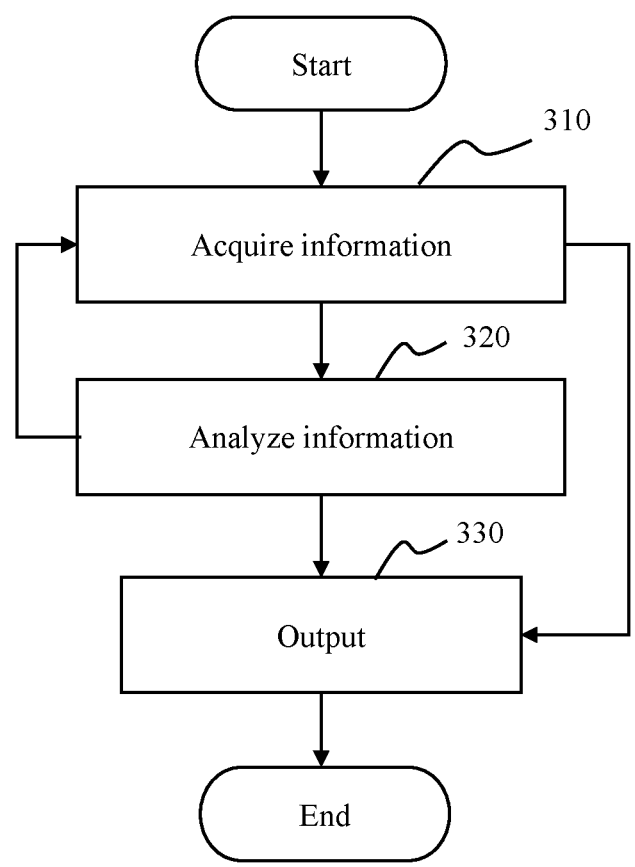
FIG. 3 is a flowchart of an exemplary process in which a method for estimating a physiological signal is deployed, according to some embodiments of the present disclosure.

FIG. 3 is a flowchart showing an exemplary process for deriving physiological features of a subject and estimating blood pressure of the subject according to some embodiments of the present disclosure. Information regarding the subject may be acquired in step 310. The information acquisition may be performed by the information acquisition module 210. The acquired information may include physiological information of the subject, environmental information relating to the ambient surrounding the subject at or around the acquisition time, information provided by the subject or a user other than the subject. The acquired information may include a PPG signal, an ECG signal, a pulse rate, a heart rate, a heart rate variation, blood oxygen saturation, respiration, muscle state, skeleton state, a brainwave, a blood lipid level, a blood sugar level, the height, the weight, the age, gender, the body temperature, the arm length, an illness history, the room temperature, humidity, air pressure, an air flow rate, the ambient light intensity, or the like, or a combination thereof. At least some of the acquired information may be analyzed at 320. Via the analysis, various features of at least some of the acquired information may be identified. For example, the acquired information may include a PPG signal and an ECG signal; the identified features of these signals may include, for example, waveform, characteristic points, peak points, valley points, amplitude, time intervals, phase, frequencies, cycles, or the like, or a combination thereof. Analysis based on the identified features may be carried out in step 320. For example, the physiological quantity of interest may be calculated or estimated based on the identified features. The physiological quantity of interest estimated based on the acquired PPG signal and ECG signal may include, for example, the mean, absolute mean, variance, standard deviation, and/or median, of the BP, the SBP, the DBP, the blood oxygen level, or the like, or a combination thereof. The physiological quantity of interest may be used for selecting a personalized model for the subject. The model may be used to calculate the blood pressure of the subject. Then the information regarding the blood pressure of the subject, for example the BP, the SBP, the DBP, the blood oxygen level, or the like, or a combination thereof, may be outputted in step 330. Some of the acquired information may be outputted in step 330 as well. The output may be displayed to the subject or a user other than the subject, printed, stored in a storage device or the server 120, transmitted to a device further process, or the like, or a combination thereof. It should be noted that after analysis in step 320, a new acquisition step may be performed in step 310.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a pre-processing step may be added between step 310 and step 320. In the pre-processing step, the acquired signals may be pre-processed, in order to reduce or remove noise or interferences in the signals originally acquired. For example, a sophisticated, real-time digital filtering may be used to reduce or remove high-frequency noise from the PPG or ECG signal, allowing their features to be accurately identified. Exemplary pre-treatment methods may include low-pass filtering, band-pass filtering, wavelet transform, median filtering, morphological filtering, curve fitting, Hilbert-Huang transform, or the like, or a combination thereof. Descriptions regarding methods and systems for reducing or removing noise from a physiological signal, for example, a PPG signal or an ECG signal, may be found in, for example, International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference. One or more other optional steps may be added between step 310 and step 320, or elsewhere in the exemplary process illustrated in FIG. 3. Examples of such steps may include storing or caching the acquired information.

Figure 4:
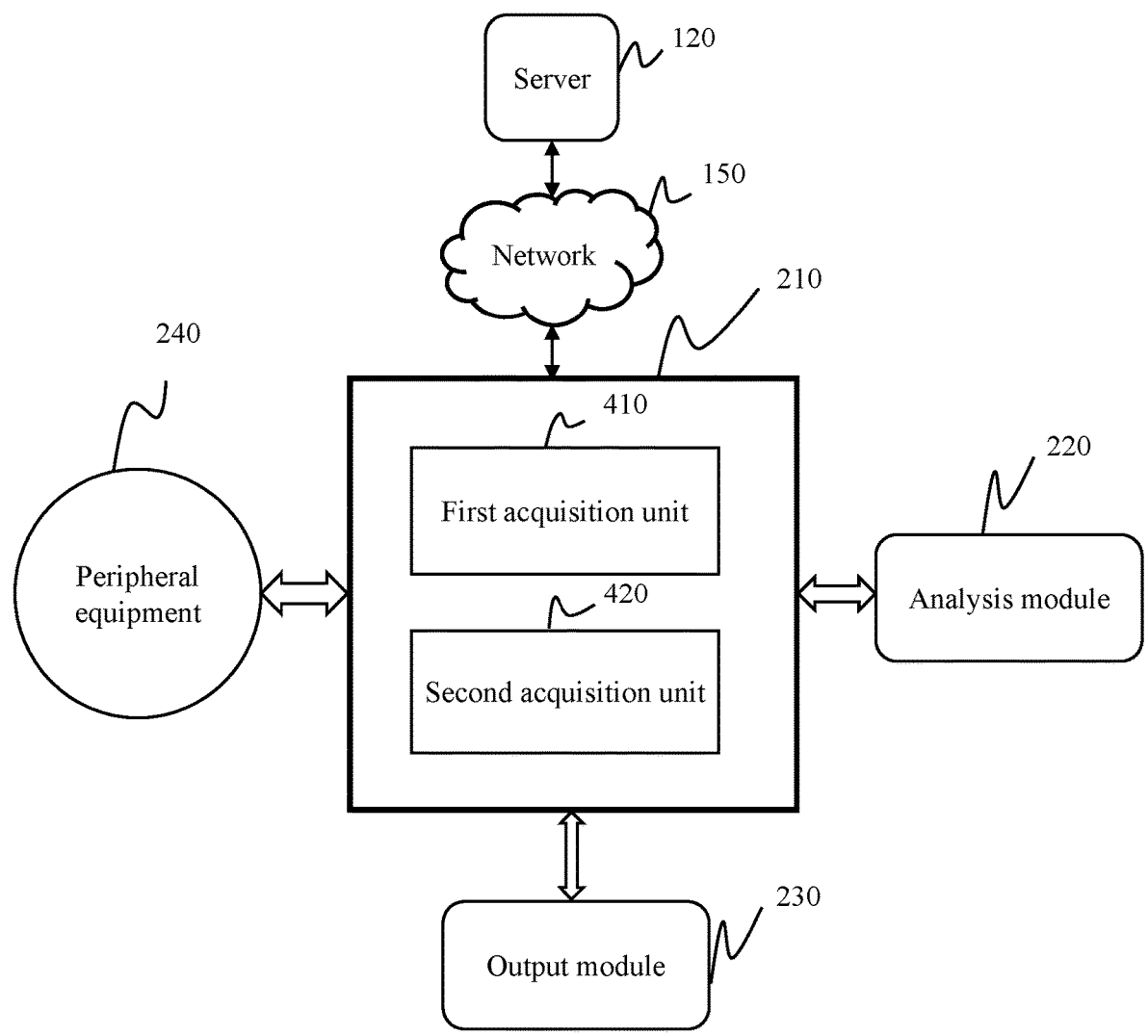
FIG. 4 is a block diagram illustrating an architecture of an information acquisition module according to some embodiments of the present disclosure.

FIG. 4 is a block diagram illustrating an architecture of an information acquisition module according to some embodiments of the present disclosure. The information acquisition module 210 may be connected to or otherwise communicate with, for example, the peripheral equipment 240, the analysis module 220, the output module 230, and the server 120 through the network 150. The information acquisition module 210 may be configured for acquiring information relating to the subject, information provided by the subject, a user other than the subject, and/or a related third party (for example, a doctor, a healthcare worker, a medical institution, a research facility, a peripheral device of the subject or a user well-connected to the subject, or the like), environmental information from the ambient surrounding the subject at or around the acquisition time, or the like, or a combination thereof. The information acquisition module 210 may include a first acquisition unit 410 and a second acquisition unit 420. The first acquisition unit 410 may be configured for acquiring a first signal or first information including a first signal relating to the subject. The second acquisition unit 420 may be configured for acquiring a second signal or second information including a second signal relating to the subject. The first acquisition unit 410 and the second acquisition unit 420 may acquire signals in real time. The first signal and the second signal may be acquired simultaneously, at or around the same time. In some embodiments, other than the first acquisition unit 410 and the second acquisition unit 420, the information acquisition module 210 may include one or more other acquisition units (not shown in FIG. 4). In some embodiments, the first acquisition unit 410 and the second acquisition unit 420 may be integrated in an independent module or unit.

In some embodiments, the first acquisition unit 410 may be configured for acquiring an ECG signal of the subject. The first acquisition unit 410 may include an ECG monitor (not shown in FIG. 4). The ECG monitor (not shown in FIG. 4) may be of any type, e.g., a clinical device, a house device, a wearable device, a portable device, or the like. The ECG monitor (not shown in FIG. 4) may include a plurality of electrodes used for recording the variations in the electrical potential relating to the cardiovascular activity of the subject. The electrodes may be arranged in a 12-lead form, a 5-lead form, a 3-lead form, or the like. The electrodes may be located on one or more limbs and/or on the chest of the subject. For instance, in the 5-lead form, the electrodes may be located on the chest of the subject. In some embodiments, the first acquisition unit 410 may include a control unit (not shown in FIG. 4). The control unit (not shown in FIG. 4) may be configured for controlling a feature of the acquisition process. The feature may include sampling frequency, sampling time interval, or the like, or a combination thereof. In some embodiments, the first acquisition unit 410 may include a storage unit (not shown in FIG. 4). The storage unit (not shown in FIG. 4) may be used for storing the acquired first signals, the features, or the like, or a combination thereof. In some embodiments, the acquired signals, the features may be stored in any storage device disclosed anywhere in the present disclosure.

In some embodiments, the second acquisition unit 420 may be configured for acquiring a PPG signal or acquiring information including a PPG signal. In some embodiments, the second acquisition unit 420 may include a blood oxygen monitor (not shown in FIG. 4). The blood oxygen monitor (not shown in FIG. 4) may be configured for acquiring the subject's blood oxygen information using a photoelectric sensor. Blood oxygen information may be estimated based on two or more PPG signals. In some embodiments, at least one of the acquired PPG signals together with an ECG signal may be used for calculating physiological features, which may be used to estimate a blood pressure value based on a personalized model.

In some embodiments, the blood oxygen monitor (not shown in FIG. 4) may include a single photoelectric sensor, or a sensor array including a plurality of photoelectric sensors. A photoelectric sensor may include one or more emitting ends and one or more receiving ends. The emitting end may include one or more light sources. A light source may emit one or more of ultrasound, radio, microwave, millimeter wave, infrared, visible, ultraviolet, gamma ray, or X-ray electromagnetic radiation. As used herein, light may also include any wavelength within the radio, microwave, infrared (IR), visible, ultraviolet (UV), or X-ray spectra, and that any suitable wavelength of electromagnetic radiation may be appropriate for use with the system, device, or apparatus disclosed herein. Merely by way of example, an emitting end may include two light sources, a red light emitting light source such as a red light emitting diode (LED), and an IR light emitting light source such as IR LED; the emitting end may emit light into the tissue of a subject at the wavelengths used to calculate a physiological feature of interest of the subject (e.g., blood oxygen information). As used herein, for brevity, a specific wavelength may also include wavelengths within a range of the specific wavelength. For instance, the red wavelength may be between approximately 600 nm and approximately 700 nm, and the IR wavelength may be between approximately 800 nm and approximately 700 nm. In embodiments where a sensor array is used, each sensor may emit a single wavelength. The receiving end may be used for receiving signals resulting from the emitted lights through the subject. In some embodiments, the second acquisition unit 420 may be configured for acquiring the subject's PPG signals from multiple body locations (for example, the head, the neck, the chest, the abdomen, the upper arm, the wrist, the waist, the upper leg, the knee, the ankle, or the like, or a combination thereof). In some embodiments, one or more photoelectric sensors may be placed on any one of the multiple body locations. In some embodiments, one or more photoelectric sensor arrays may be placed on any of the multiple body locations.

In some embodiments, the second acquisition unit 420 may include a control unit (not shown in FIG. 4) and/or a storage unit (not shown in FIG. 4). Similarly the control unit (not shown in FIG. 4) may be configured for controlling the acquisition process of the second signal or second information. The storage unit (not shown in FIG. 4) may be configured for storing the acquired signals and/or information.

The information acquisition module 210 may include one or more other acquisition units (not shown in FIG. 4). For example, an acquisition unit may be configured for acquiring basic information relating to the subject, for example, the height, the weight, the age (or the date of birth), the gender, the arm length, the nationality, the occupation, a habit (for example, a health-related habit such as an exercise habit), the education background, a hobby, the marital status, religious belief, a health-related history (for example, whether a subject has a history of smoking, a food allergy, a drug allergy, a medical treatment history, a family health history, a history of genetic disease, information regarding a prior surgery, or the like, or a combination thereof), contact information, emergency contact, or the like, or a combination thereof. The basic information relating to the subject may be provided by the subject, a user other than the subject, or a third party (for example, a doctor, a healthcare worker, a medical institution, a research facility, a peripheral device of the subject or a user well-connected to the subject, or the like).

In another example, an acquisition unit may be configured for acquiring environmental information surrounding the subject, including temperature, humidity, air pressure, an air flow rate, an ambient light intensity, or the like, or a combination thereof. The environmental information may be acquired in a real time mode (for example, at or around the acquisition time), or may be acquired at a certain time interval (for example, independent of the acquisition time).

In a further example, one or more acquisition units may be configured for acquiring the subject's EMG signals by way of a pressure sensing method, body temperature data by way of a temperature sensing method, or the like, or a combination thereof. In a further example, an acquisition unit may be configured for acquiring BCG signals, blood density information, pH value information of the blood, or the like, or a combination thereof.

The one or more acquisition units may communicate with one or more sensors to acquire information sensed, detected or measured by the one or more sensors. Exemplary sensors include an electrode sensor, an optical sensor, a photoelectric sensor, a conductance sensor, a pressure sensor, an accelerometer, a gravity sensor, a temperature sensor, a moisture sensor, or the like, or a combination thereof.

Merely by way of example, an optical sensor may include an integrated photodetector and a light source. The optical sensor may also include an amplifier. The light source may emit radiation of wavelengths of, for example, the visible spectrum, the infrared region, or the like, or a combination thereof. The photodetector may detect the radiation resulting from light (of a wavelength, or within a range of the wavelength) that impinges upon or into and/or is reflected by a tissue, and reaches the photodetector (or referred to as the reflected radiation). The optical sensor may be placed at a body location of a subject to detect a pulse-related signal of a subject. For instance, the optical sensor may be a PPG sensor. In some embodiments, an optical sensor may include a plurality of light sources, in which a light source may emit light of a wavelength, or within a range of the wavelength. Thus, the plurality of light sources may emit light of various wavelengths, or within a respective range thereof. For instance, the light sources may emit a red light and an infrared light. In some embodiments, an optical sensor may include a plurality of photodetectors, in which a photodetector may be used to detect the reflected radiation resulting from the light of a wavelength, or within a range of the wavelength. In some embodiments, a photodetector may be used to detect the reflected radiation resulting from the emitted light of various wavelengths, or within a respective range thereof. For instance, a photodetector may be used to detect the reflected radiation resulting from the red light and the infrared light.

In some embodiments, a plurality of PPG sensors may be assembled into one device. One PPG sensor of the plurality of PPG sensors may include a light source, and a photodetector; the light source may emit light of a wavelength, or within a range thereof; the photodetector may be used to detect the reflected radiation resulting from the emitted light (of a wavelength, or within a range of the wavelength). The plurality of PPG sensors may include a PPG sensor that includes a red light emitting light source and a photodetector that may detect the reflected radiation resulting from the red light, and a PPG sensor that includes an infrared light emitting light source and a photodetector that may detect the reflected radiation resulting from the infrared light. In some embodiments, at least two of the plurality of PPG sensors may be placed at different locations on the body of a subject. For instance, one PPG sensor may be placed on an upper arm of the subject, and another PPG sensor may be placed on a finger of the subject. In some embodiments, at least two of the plurality of PPG sensors may be placed at or around the same location on the body of a subject. For instance, two PPG sensors may be placed at an upper arm of the subject. In another example, two PPG sensors may be placed at a finger of the subject. In some embodiments, a device may include a PPG sensor; the PPG sensor may include a plurality of light sources and a photodetector; the light sources may emit light of various wavelengths, or within a respective range thereof; the photodetector may be used to detect the reflected radiation resulting from the emitted light of various wavelengths, or within a respective range thereof.

The device may be a wearable or portable device including, for example, a T-shirt, a smart watch, a wristband, or the like, or a combination thereof. The device may further include one or more processors or processing units. The processor or the processing unit may be configured for controlling the process of information acquisition, or may be configured for performing one or more operations of any of the modules. Signals or data may be transmitted between sensors placed at different locations. The transmission may be via a wireless connection (for example, WiFi, blue tooth, near-field communication (NFC), or the like, or a combination thereof), a wired connection, or the like, or a combination thereof. For example, signals received by the sensors may be transmitted through a wireless body sensor network (BSN) or an intra-body communication (IBC).

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the acquisition units may be integrated into an independent unit configured for acquiring more than one information or signal relating to the subject. At least some of the acquisition units may be integrated into one or more independent units. The one or more acquisition units may share a common control unit (not shown in FIG. 4) and/or a common storage unit (not shown in FIG. 4).

Figure 5:
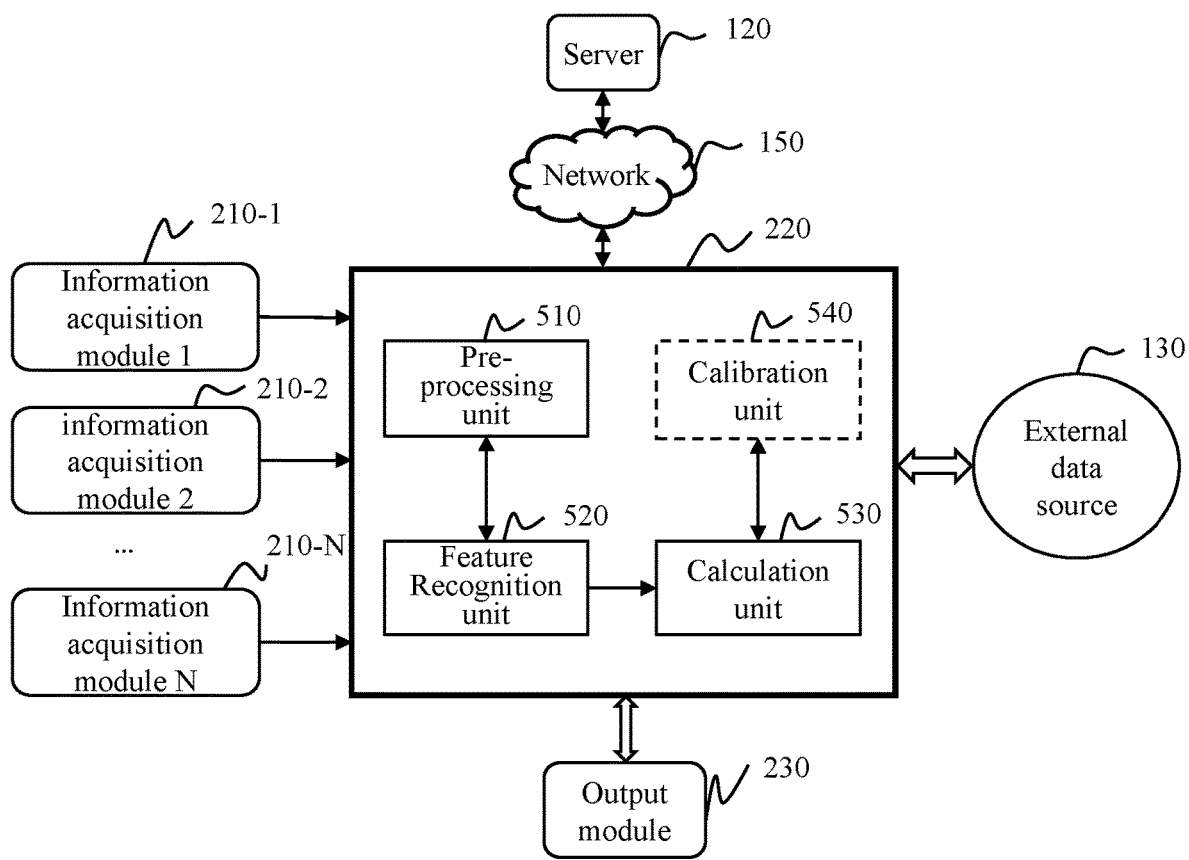
FIG. 5 is a block diagram illustrating an architecture of an analysis module according to some embodiments of the present disclosure.

FIG. 5 is a block diagram illustrating an architecture of an analysis module according to some embodiments of the present disclosure. The analysis module 220 may be connected to or otherwise communicate with, e.g., the peripheral equipment 240, and the server 120 through the network 150. The analysis module 220 may estimate or calculate blood pressure relating to a subject based on acquired information. The analysis module 220 may include a pre-processing unit 510, a feature recognition unit 520, a calculation unit 530, and possibly a calibration unit 540.

The pre-processing unit 510 may be configured for pre-processing the acquired information. The pre-processing may be performed to reduce or remove noise or errors in the original signals. In some embodiments, a correction of standard deviation for the PPG waveforms may be performed by the pre-processing unit 510. For example, for a PPG waveform consisting of tens of heart beating period, the average, median value, and/or the standard deviation of the maximum/minimum value of the PPG waveform within each heart beating period may be calculated. A threshold may be specified to designate the outliers within the PPG waveforms. For example, a threshold of value 0.1 may be set. If the standard deviation of the maximum/minimum value of the PPG waveform within each heart beating period is less than the threshold, then the PPG waveform may be labelled as outliers and disposed of. Similarly, the pre-processing unit 510 may process the personal data of the subject. A trusted interval for the values of the personal data may be set. Any personal data outside of the trusted interval may be labelled as questionable and needs to be corrected. For example, if the height of the subject is 5 cm, and/or the weight of the subject is 5 kilograms, then the personal data of the subject may be labelled as questionable and needs to be corrected. Exemplary methods for pre-treatment may include low-pass filtering, band-pass filtering, wavelet transform, median filtering, morphological filtering, curve fitting, Hilbert-Huang transform, or the like, or any combination thereof. Descriptions regarding methods and systems for reducing or removing noise from a physiological signal, e.g., a PPG signal or an ECG signal, may be found in, e.g., International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference.

In some embodiments, the physiological features obtained in the feature recognition unit 520 may be transferred to the pre-processing unit 510 for treatment of outliers. For example, a PPG waveform of a subject may be designated as training data. A collection of training data may be stored in the database 73. The physiological features of the PPG waveform may be obtained in the feature recognition unit 520 and transferred to the pre-processing unit 510. The pre-processing unit 510 may calculate Cook's Distance for the physiological features of the PPG waveform. If the Cook's Distance is larger than C/N, then the PPG waveform as training data may be disposed of. Here N is the number of training data, C is a pre-determined value. In some embodiments, C may be chosen as an integer larger or equal to 4.

Figure 6:
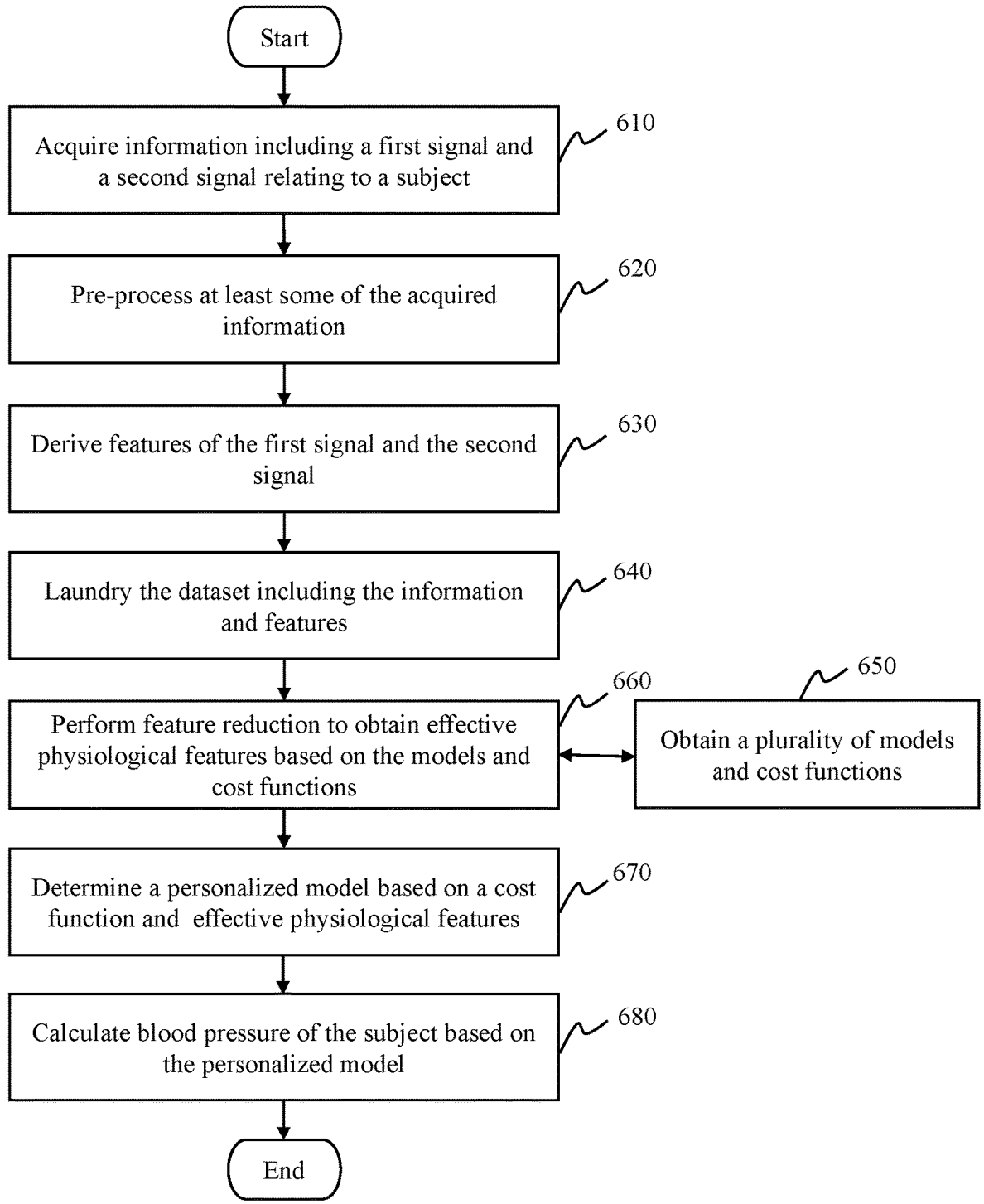
FIG. 6 is a flowchart of a process for determining a personalized model and calculating blood pressure of a subject according to some embodiments of the present disclosure.

The pre-processing unit 510 may include one or more pre-processing sub-units (not shown in FIG. 6). The pre-processing sub-units may (not shown in FIG. 6) perform one or more pre-processing steps for pre-processing the acquired signals in series (e.g., a pre-treatment step performed after another pre-treatment step has commenced or completed) or in parallel (e.g., some pre-treatment steps performed at or around the same time). The pre-treatment unit 510 may control or coordinate the operations of the pre-processing sub-units (not shown in FIG. 6). The control or coordination may be performed by, e.g., a controller within the pre-processing unit 510 (not shown in FIG. 6) or a controller outside of the pre-processing unit 510. The pre-processing sub-units may be arranged in series or in parallel.

This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the pre-treatment sub-units may be combined variously in order to achieve better pre-treatment effect. It should be noted that the pre-treatment sub-units are not necessary for the function of the system. Similar modifications should fall within the metes and bounds of the claims.

The recognition unit 520 is configured for analyzing the acquired information to recognize or identify a feature. In some embodiments, the acquired information may have been pre-processed before it is processed in the recognition unit 520. In the exemplary context of blood pressure monitoring, the acquired information may include a PPG signal, an ECG signal, a BCG signal, or the like, or a combination thereof; exemplary features of the acquired information may include characteristic points, peak points, valley points, amplitude, time intervals, phase, frequencies, cycles, ratio, maximum slope, starting time, ending time, direct current (DC) component, alternating current (AC) component, or the like, or any combination thereof, of a function of the PPG waveform. The function of the waveform may be identical function, or the first derivative or higher order derivatives of the waveform.

The recognition unit 520 may be configured for analyzing different types of information or different portions of information. The analysis may be performed by, e.g., one or more recognition sub-units (not shown in FIG. 6). For example, the acquired information includes various types of physiological signals (e.g., a PPG signal and an ECG signal) and may be analyzed by different recognition sub-units. Exemplary methods that may be employed in the recognition unit 520 may include a threshold method, a syntactic approach of pattern recognition, Gaussian function depression, wavelet transform, a QRS complex detection, a linear discriminant analysis, a quadratic discriminatory analysis, a decision tree, a decision table, a near neighbor classification, a wavelet neural networks model, a support vector machine, gene expression programming, hierarchical clustering, a mean cluster analysis, a Bayesian network model, a principal component analysis, a Kalman filter, Gaussian regression, linear regression, Hidden Markov Model, association rules, an inductive logic method, or the like, or any combination thereof. Various methods may be used in parallel or may be used in combination. Merely by way of example, the recognition unit may use two different methods when processing two types of signals. As another example, the recognition unit may use two different methods, e.g., one method after another, when processing one type of signal.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. Merely by way of example, the analyzed features may be uploaded to the public clouds or the personal clouds and may be used in subsequent calculation or calibration. As another example, the recognition sub-units (not shown in FIG. 6) are not necessary for the function of the system. Similar modifications should fall within the metes and bounds of the present disclosure.

The calculation unit 530 may be configured for performing various calculations to determine, e.g., coefficients of a model or function relating to a physiological feature of interest, mean, median value, and/or standard deviation of calculated blood pressure, or the like, or a combination thereof. In some embodiments, the calculation unit 530 may try to reduce the number of physiological features based on a personalized model for a subject. For example, the calculation unit 530 may calculate the Akaike information criterion (AIC) value based on the physiological features and the model selected for the subject. If the AIC value decreases after a physiological feature F1 is removed from the set of physiological features, then the physiological feature F1 may be disposed of from the set of physiological features. The process of disposing of physiological features may be stopped when the AIC value increases. The physiological features left after the process of disposing of physiological features may be referred to as "effective physiological features". The calculation unit 530 may include one or more calculation sub-units (not shown in FIG. 6) to perform the calculations. A physiological feature of interest may including, e.g., PTT, PTTV (pulse transit time variation), a BP, a SBP, a DBP, a pulse rate, a heart rate, a HRV, cardiac murmur, blood oxygen saturation, a blood density, a blood oxygen level, or the like, or any combination thereof.

Exemplary methods that may be employed in the calculation unit 530 may include a direct mathematical calculation, an indirect mathematical calculation, a compensated calculation, a vector operation, a function operation, a wave speed evaluation, an equation feature evaluation, a tension evaluation, or the like, or any combination thereof. One or more calculation models may be integrated in the calculation sub-units, or the calculation models may be placed in the server 120, or the calculation models may be placed in public clouds. Different models may be loaded when different coefficients or physiological features are to be calculated. For example, a linear calculation model in a calculation sub-unit may be used for calculating the SBP, while another non-linear calculation model in another calculation sub-unit may be used for calculating the DBP. An initial data or intermediate result used for calculating a physiological feature of interest may be retrieved or loaded from the information acquisition module 210, the analysis module 220, the server 120, the external data source 130, the peripheral equipment 240, or the like, or any combination thereof. The external data source 130 may include information from medical institution 131, research facility 132, database 133, and peripheral device 134. The initial data and the intermediate result may be combined in various ways in the calculation unit 530.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. In one embodiment, calculated coefficients or calculated physiological features may be used as an intermediate result for further analysis. In another example, an individual physiological feature of interest or one group of related physiological features of interest may be calculated by the calculation unit.

The calibration unit 540 may be configured for performing a calibration. The calibration (also referred to as calibration process or calibration procedure) may include one or more steps of retrieving calibration data (or calibration values) for a subject; acquiring a set of information of the subject using a device to be calibrated or used in a future process (e.g., a wearable or portable device); determining a calibrated model or a portion thereof for the calibrated device with respect to the subject, or the like, or a combination thereof. The acquired set of information may include information provided by the subject or a user other than the subject, or information acquired by using the device to be calibrated, or the like, or a combination thereof. A set of calibration data may include a specific physiological feature of interest obtained in one calibration process, an acquired set of information relating to the specific physiological feature of interest in the same calibration process.

Merely by way of example, the device to be calibrated may calculate blood pressure (including the SBP and the DBP) based on personalized model selected for a subject and effective physiological features. In some embodiments, the device to be calibrated may be a portion of the system other than the calibration unit 540. A set of calibration data may include a SBP and a DBP, both measured by a healthcare provider in a hospital setting, and a corresponding ECG waveform and a corresponding PPG waveform acquired using the device to be calibrated. The corresponding ECG waveform and the corresponding PPG waveform acquired using the device to be calibrated may correspond to the SBP and the DBP measured by a healthcare provider. The corresponding ECG waveform and the corresponding PPG waveform may be acquired using the device to be calibrated at or around the time the SBP and the DBP are measured by a healthcare provider.

In some embodiments, a set of calibration data may include a SBP, a DBP, and a corresponding ECG waveform and a corresponding PPG waveform, all acquired using the device to be calibrated. For instance, the calibration unit 540 may include or communicate with a cuff-based blood pressure monitor. The cuff-based blood pressure monitor may be integrated into the system or device, or a portion thereof (e.g., the calculation unit, the information acquisition module, or the like). For instance, a cuff-based blood pressure monitor, an ECG monitor that may acquire ECG information, and one or more PPG sensors may be packaged into a device, or a system, or a portion thereof. The cuff-based blood pressure monitor may measure a SBP and a DBP at a certain time interval (e.g., 15 min, 30 min, 1 hour, 2 hour, a day, or the like). The set of calibration data may be acquired automatically based on a default setting of the system, or preset instructions by the subject or a user other than the subject (also referred to as a third party). Exemplary third parties may be a doctor, a healthcare worker, a medical institution, a research facility, a peripheral device of the subject or a user well-connected to the subject, or the like. The set of calibration data acquired by the calibration unit 540 may be transmitted to the calculation unit 530 or other modules or units in real time. The set of calibration data may be stored in a storage device disclosed anywhere in the present disclosure or may be stored in the server 120. If needed, the set of calibration data may be loaded from the storage device or the server 120 automatically.

One or more sets of calibration data may be used to determine coefficients of a calibrated model, or some other portion(s) of the calibrated model. The calibrated model may be used in a future process for calculating the physiological feature of interest based on another set of information that is acquired using the calibrated device. In a future process, the calibrated device may acquire a set of information that is the same or similar to the set of information acquired for the calibration. For instance, the other set of information may include information acquired using the same device as that used in the calibration (e.g., the device including one or more sensors), information of the same type as that acquired in the calibration (e.g., the age of the subject, the acquisition time during the day, the physiological or psychological condition of the subject, or the like, or a combination thereof), or the like, or a combination thereof. The calibrated model may be used to calculate or estimate the physiological feature of interest accordingly. Exemplary methods that may be used in the calibration to obtain the calibrated model may include a regression analysis, a linear analysis, a functional operation, reconstitution, Fourier transform, Laplace transform, or the like, or a combination thereof.

In a calibration process, a set of calibration data may include a specific physiological feature of interest obtained based on a measurement using one or more devices other than the device to be calibrated. Merely by way of example, the specific physiological feature of interest may be obtained based on a measurement performed on the subject by the calibration unit 540 (e.g., a cuff-based blood monitor). As another example, the specific physiological feature of interest may be obtained based on a measurement performed on the subject by a healthcare professional in a hospital or a doctor's office. As another example, the specific physiological feature of interest may be obtained based on a measurement performed on the subject by the subject or someone else using a clinical device or a household device. For instance, the physiological feature of interest may be measured using a device including, e.g., an auscultatory device, an oscillometric device, an ECG management device, a PPG management device, or the like, or any combination thereof.

In a calibration process, a set of calibration data may include a specific physiological feature of interest previously calculated or estimated by the system or a portion of the system. Merely by way of example, the physiological feature of interest calculated by the system based on a set of acquired information and a calibrated function in the system may be used in a next calibration to update or generate a calibrated model, and the updated calibrated model may be used in the future to calculate the physiological feature of interest (the first aspect of the calibration process described above). As another example, the physiological feature of interest calculated by the system based on a set of acquired information and a calibrated function in the system may be used in a next measurement for the physiological feature of interest (the second aspect of the calibration process described above). The calculated physiological feature of interest of the subject may be stored in a storage device disclosed anywhere in the present disclosure or in the server 120, for future use in connection with the subject or other subjects.

In the exemplary context of estimating BP of a subject (including SBP and DBP), based on PTT, the correlation between BP and PTT may be represented by a model including mathematical processing, and a factored function, while the factored function may include a function ($f$) and coefficient (B). As used herein, a calibration may include at least two aspects. A first aspect is that a model is determined based on one or more sets of calibration data (or calibration values). The determined model may be referred to as a calibrated model. To use the calibrated model in a specific measurement, signals need to be acquired to provide PTT, and a set of calibration data including PTT0, SBP0, and DBP0. The correlation between BP and PTT may depend on other elements, in addition to PTT. Merely by way of example, the correlation between BP and PTT may depend on HRV, PTTV, in addition to PTT. To use the calibrated model in a specific measurement, signals need to be acquired to provide PTT, HRV, and PTTV, and a set of calibration data including PTT0, SBP0, DBP0, HRV0, and PTTV0.

The first aspect of calibration may be performed using personalized calibration data relating to the subject, or peer data, or empirical data. This aspect of calibration may be performed real time when a specific measurement is performed. A model to be used to estimate BP based on the PTT in the specific measure may be derived based on one or more sets of calibration data. The selection of the one or more sets of calibration data may be based on the PTT in the specific measurement. This aspect of calibration may be perform offline, independent of a specific measurement.

A second aspect of the calibration includes acquiring a set of calibration data to be applied in a calibrated model so that a blood pressure may be estimated based on PTT acquired in a specific measurement, according to the model and the set of calibration data. In some embodiments, the set of calibration data to be used in the specific measurement may be selected from, e.g., a plurality of sets of calibration data. The plurality of sets of calibration data may include personalized data relating to the subject, peer data, or empirical data. The plurality of sets of calibration data may be saved in the system, e.g., in the library 900 (see FIG. 1). The plurality of sets of calibration data may be saved in a server that is part of or accessible from the system. In some embodiments, the set of calibration data may be selected based on the PTT in the specific measurement.

A calibrated model to be used for a specific subject may be based on the calibration data of the same subject. A calibrated model to be used for a specific subject may be based on a combination of the calibration data of the same subject and calibration data from a group of subjects (e.g., peer data discussed elsewhere in the present disclosure). A calibrated model to be used for a specific subject may be based on the calibration data from a group of subjects (e.g., peer data or empirical data discussed elsewhere in the present disclosure). The specific subject may be included in the group, or not included. The calibration data may be stored in a storage device disclosed anywhere in the present disclosure or the server 120, or the like, or a combination thereof. Personalized calibration data of different subjects may be stored in corresponding personal accounts of respective subjects in the server 120 or a personal cloud. Calibration data from various subjects may be stored in a non-personalized database for future use. For instance, calibration data from various subjects may be divided based on one or more characteristics of the respective subjects. Exemplary characters may include, e.g., age, gender, stature, weight, a body fat percentage, color of skin, a family health history, a life style, an exercise habit or other habit, diet, a psychological condition, a health condition, an education history, occupation, or the like, or a combination thereof. In some embodiments, a portion of the calibration data (e.g., peer data discussed elsewhere in the present disclosure) so divided may be used for calibration purposes by a group of subjects that share the same or similar characteristic(s).

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a storage unit (not shown in FIG. 6) may be added to the calibration unit 540 or the calculation unit 530, or a combination thereof. The storage unit in the calibration unit 540 may store the calibration data or historical data relating to calibration process. The storage unit relating to calculation unit 530 may store calculation models or data relating to calculation process. Additionally, peer data may be used as initial data or an intermediate result during calibrating.

The analysis module 220 may be implemented on one or more processors. Various units of the analysis module 220 may be implemented on one or more processors. For example, the pre-treatment unit 510, the recognition unit 520, the calculation unit 530, and the calibration unit 540 may be implemented on one or more processors. The one or more processors may transmit signals or data with a storage device (not shown in FIG. 6), the information acquisition modules 1, 2, and 3, the peripheral equipment 240, and the server 120. The one or more processors may retrieve or load signals, information, or instructions from the storage device (not shown in FIG. 6), the information acquisition modules 1, 2, and 3, the peripheral equipment 240, or the server 120, and process the signals, information, data, or instructions, or a combination thereof, to perform pre-treatment, calculation of one or more physiological features of interest, calibration, or the like, or a combination thereof. The one or more processors may also be connected or communicate with other devices relating to the system 100, and transmit or share signals, information, instructions, the physiological features of interest, or the like with such other devices via, e.g., a mobile phone APP, a local or remote terminal, or the like, or a combination thereof.

FIG. 6 is a flowchart diagram of an exemplary process for estimating blood pressure according to some embodiments of the present disclosure. Beginning in step 610, information including a first signal and a second signal may be acquired. For example, the first signal may be a ECG signal, and the second signal may be a PPG signal. The first signal and second signal may be related to a subject. The acquisition of the signals may be performed by the information acquisition module 210. In some embodiments, the first and second signals may be acquired simultaneously, at or around the same time. In some embodiments, one signal may be acquired prior to the other signal. In some embodiments, information including or relating to the first signal or the second signal may be acquired in step 610. For instance, information about personal data of the subject, such as the age, weight, height, and historical medical record, may be acquired. As another example, basic information relating to the subject and/or environmental information may be acquired.

Merely by way of example, the first signal or the second signal may be physiological signals, e.g., an electrocardiogram (ECG) signal, a pulse-wave-related signal (such as photoplethysmogram (PPG)), a phonocardiogram (PCG) signal, an impedance cardiogram (ICG) signal, or the like, or any combination thereof. In some embodiments, the first signal and the second signal may be of different types. For example, the first and second signals may be the combination of an ECG signal and a PPG signal, the combination of an ECG signal and a PCG signal, the combination of an ECG signal and an ICG signal, or the like. In some embodiments, the first signal and the second signal may be of the same type. For example, the first and second signals may be two PPG signals that may be detected at different locations on the body of the subject. The exemplary locations on the body of the subject may include, e.g., the finger, the radial artery, the ear, the wrist, the toe, or the locations that are more suitable for ambulatory monitoring in current sensor designs.

In step 620, at least some of the acquired information may be pre-processed. In some embodiments, the acquired first and second signals may be pre-processed. The pre-processing may be performed to reduce or remove noise or errors in the signals or signal related data. Exemplary methods that may be used in the pre-treatment may include low-pass filtering, band-pass filtering, wavelet transform, median filtering, morphological filtering, curve fitting, Hilbert-Huang transform, or the like, or any combination thereof. During the process of the pre-processing, the methods mentioned herein may be used in parallel or may be used in combination. Descriptions regarding methods and systems for reducing or removing noise from a physiological signal, e.g., a PPG signal or an ECG signal, may be found in, e.g., International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference. Additionally, real-time transformation of time domain or frequency domain may also be implemented in step 820, and the signals or related information may be used in time domain, frequency domain, wavelet domain, or all of them.

In step 630, the features of the first and second signals may be recognized or identified. In the exemplary context of blood pressure monitoring, the first signal or the second signal may include a PPG signal, an ECG signal, a BCG signal, or the like; exemplary features of the first signal or the second signal may include characteristic points, peak points, valley points, amplitude, time intervals, phase, frequencies, cycles, ratio, maximum slope, starting time, ending time, direct current (DC) component, alternating current (AC) component, or the like, or any combination thereof, of a function of the PPG waveform. The function of the waveform may be identical function, or the first derivative or higher order derivatives of the waveform. For example, one characteristic point may be a peak or a valley of the first signal, e.g., the peak or valley of R wave of an ECG signal, a fastest rising point of a PPG signal, a higher order moment or a higher order derivative of the PPG signal, a pulse area of the PPG signal, a maximum positive peak of S2 of a PCG signal, or a peak of an ICG signal, or the like.

In step 640, a dataset including the physiological features identified and the personal data of the subject may be cleaned. By cleaning the dataset we mean the outliers within the dataset may be removed or corrected. For example, for a PPG waveform consisting of tens of heart beating period, the average, median value, and/or the standard deviation of the maximum/minimum value of the PPG waveform within each heart beating period may be calculated. A threshold may be specified to designate the outliers within the PPG waveforms. If the standard deviation of the maximum/minimum value of the PPG waveform within each heart beating period is less than the threshold, then the PPG waveform may be labelled as outliers and disposed of. Similarly, the personal data of the subject may be laundered. A trusted interval for the values of the personal data may be set. Any personal data outside of the trusted interval may be labelled as questionable and needs to be corrected. For example, if the height of the subject is 5 cm, and/or the weight of the subject is 5 kilograms, then the personal data of the subject may be labelled as questionable and needs to be corrected.

A pre-treatment step may be performed to assess an acquired signal (for example, an ECG signal, a PPG signal, etc.) before one or more features of the signal is identified. For instance, an acquired ECG signal may be accessed before one or more features of the signal is identified. The assessment may be performed to evaluate whether a valid ECG signal is acquired. The assessment may be performed by way of, for example, a pattern recognition process. For instance, the R peak of an acquired ECG signal may be determined by the pattern recognition process. In some embodiments, the system may identify an abnormal signal or waveform (e.g., an abnormal sinus rhythm R wave, another physiological signal, or the like) that may be unsuitable for deriving physiological features; such an abnormal signal or waveform may be abandoned to avoid to be involved in the subsequent calculation or analysis. In some embodiments, the acquired ECG signal may be compared with a reference signal to determine whether the acquired ECG signal includes an abnormal R wave. The reference signal may be a normal sinus rhythm ECG signal, or may be retrieved from a database having historical data.

The ECG waveform and the PPG waveform are cyclical signals, i.e. the characteristic points occur substantially cyclically or periodically. Thus, during recognition of characteristic points of the PPG waveform, a threshold may be set regarding the time window or segment within which the characteristic points on the PPG waveform may be identified and used to determine physiological features. In one example, the time window may be tens of heart beating periods. Merely by way of example, an analysis to identify a fiduciary point on a PPG waveform is performed on a segment of the PPG waveform occurring within 2 seconds from the time point when the maximum point on the ECG waveform is identified, in order to obtain physiological features. As another example, an analysis to identify a fiduciary point on a PPG waveform is performed on a segment of the PPG waveform occurring between two consecutive peak points on the ECG waveform, in order to approximate the PTT. As a further example, the time window may be set based on the heart rate of the subject. For instance, the time window may be set based on the heart rate of the subject at or around the acquisition time, or an average heart rate of the subject for a period of time, or an average heart rate of a group of people (for example, a sub-group of people who share a same or similar characteristic with the subject; exemplary characteristic may include age, gender, nation, stature, weight, a body fat percentage, color of skin, a family health history, a life style, an exercise habit or other habit, diet, occupation, illness history, education background, marital status, religious belief, or the like, or any combination thereof.

The cycle of ECG or the cycle of PPG may vary. As an example, the cycle of ECG or the cycle of PPG of different subjects may be different. As another example, the cycle of ECG or PPG of the same subject may vary under different situations (e.g., when the subject is exercising or asleep, at different times of a day, at the same or similar time on different days), or the like, or a combination thereof. In one example, the time window threshold may be set based on the heart rate of a subject (for example, the cycle of average person is approximately 60-120 beats per minute). The heart rate may be an average value over a period of time (e.g., a week, a month, a year, or the like). The heart rate may be one measured at or around the acquisition time. The heart rate may be measured based on, e.g., the ECG signal, the PPG signal, or the like. The time window may be set or updated based on the measured heart rate. In another example, the time window may be set by, e.g., the system, the subject, or a user other than the subject, based on the physiological information of the subject. For example, the physiological information may include motion or not, taking medicine or not, good or bad mood, emotional stress or not, or the like, or a combination thereof. In another example, the time window may be a fixed value defined by the system, the subject, or a user other than the subject (e.g., his doctor, health care provider, or the like).

In step 650, a plurality of models and cost functions may be obtained. The models to select may be one of the following forms:

$$\widehat{Sbp} = g_{sbp}(X_1, X_2, \ldots, X_k) + R(id)$$

$$\widehat{Dbp} = g_{dbp}(X_1, X_2, \ldots, X_k) + R(id)$$

$$\widehat{bpdif} = g_{bpdiff}(X_1, X_2, \ldots, X_k) + R(id)$$

$$\widehat{lnSbp} = g_{lnsbp}(X_1, X_2, \ldots, X_k) + R(id)$$

$$\widehat{nDbp} = g_{lndbp}(X_1, X_2, \ldots, X_k) + R(id)$$

Where Sbp is the systolic pressure, Dbp is the diastolic pressure. $g_{sbp}(.)$, $g_{dbp}(.)$, $g_{bpdiff}(.)$, $g_{lnsbp}(.)$, $g_{lndbp}(.)$ are the structural components (non-random) of the predictive functions of the input physiological features, such as characteristic points of the PPG signals, demographic information of the subject. The functional relationship can be linear, non-linear, regression tree or random forest which is determined by the cost function. An example of linear function takes the following form: $g(X_1, X_2, \ldots) = \beta_0 + \beta_1 X_1 + \beta_2 X_2 \ldots$ $\beta i$ is the model coefficient to be determined, $x_i$ is the effective physiological features, i=1, 2, . . . M, where M is the number of chosen physiological features, id is the personal variable related to the subject. The structural component $g_{sbp}(.)$, $g_{dbp}(.)$, $g_{bpdiff}(.)$, $g_{lnsbp}(.)$, $g_{lndbp}(.)$ are set to be constant across general population, while R(id) denotes the random component of the predictive function, which is individual specific. In some embodiments, the structural component $g_{sbp}(.)$, $g_{dbp}(.)$, $g_{bpdiff}(.)$, $g_{lnsbp}(.)$, $g_{lndbp}(.)$ may be dependent upon the training data and/or the calibration data. The cost functions to select may be mean, median, standard deviation of the prediction errors of the test data.

In step 660, feature extraction for each model may be performed via likelihood-based principles such as the Akaike information criterion (AIC), the Bayesian information criterion (BIC), via Cross-validation methods, or via shrinkage-based methods. An optimal subset of the physiological features that will lead to minimal cross-validated prediction errors can be determined using the above methods. As a data driven approach, the elements of the optimal subset can vary depending on population (such as gender and/or age), blood pressure measuring positions, etc.

In step 670, a personalized model may be determined based on a cost function and effective physiological features obtained in step 660. For example, the cost function may be chosen as the standard deviation of prediction error of the test data. Based on the behavior of the models listed in step 650, a model with minimum standard deviation of the prediction errors of the test data may be designated as the personalized model for the subject.

In step 680, BP (blood pressure) values of the subject may be calculated based on the personalized models and effective physiological features, e.g., maximum and minimum value of the slope of the PPG pulse wave, DC (direct current) component of the PPG pulse wave, AC (alternating current) component of the PPG pulse wave, the determined PTT (pulse transit time), PTTV (pulse transit time variation) and HRV, or the like, or a combination thereof. The personalized model may include a linear function based model, a non-linear function based model, a regression tree/random forest based model.

While the foregoing has described what are considered to constitute the present disclosure and/or other examples, it is understood that various modifications may be made thereto and that the subject matter disclosed herein may be implemented in various forms and examples, and that the disclosure may be applied in numerous applications, only some of which have been described herein. Those skilled in the art will recognize that present disclosure are amenable to a variety of modifications and/or enhancements. For example, the pre-treatment step 530 may not be necessary. Additionally, a third signal may be acquired if needed, and the third signal may be a signal with the same type with the first signal or the second signal, or may be a signal different with the first signal or the second signal.

Figure 7:
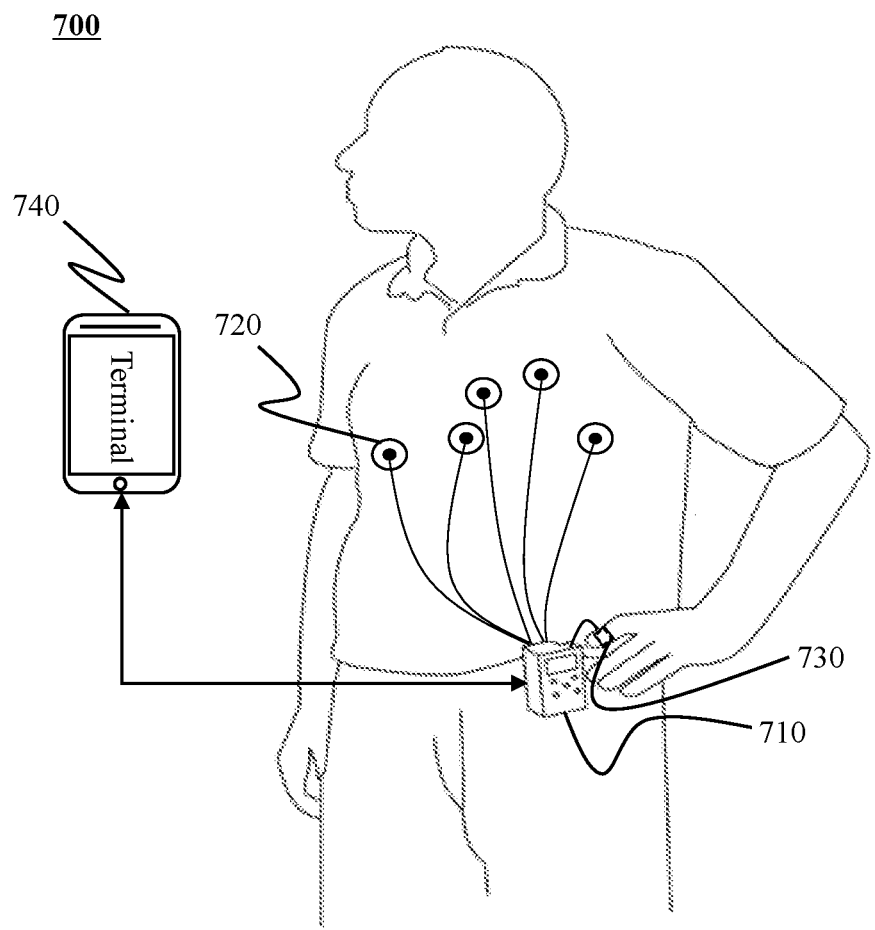
FIG. 7 illustrates an exemplary personal health manager according to some embodiments of the present disclosure.

FIG. 7 illustrates an exemplary monitoring device 700 according to some embodiments of the present disclosure. The monitoring device 700 may include a measurement module 710, an electrode 720, a finger clip 730, and/or a terminal 740. The monitoring device 700 may be connected or otherwise communicate with the terminal 740.

The measurement module 710 may be configured for acquiring information, for example, an ECG signal, a PPG signal, blood oxygen information, or the like, or a combination thereof. The measurement module 710 also may be configured for analyzing and processing the acquired information, or determining or estimating a physiological feature of interest, or determining blood pressure, or the like.

According to the embodiment, the measurement module 710 includes an ECG acquisition unit configured for acquiring ECG signals by way of electric sensing method, and a PPG signal acquisition unit configured for acquiring PPG signal related information by way of photoelectric sensing method. The acquired signals or information may be stored in the server 120, or a storage device (not shown in FIG. 7) integrated in the measurement module 710, or any storage device disclosed anywhere in the present disclosure.

The monitoring device 700 may be a wearable device, a portable device, a medical monitoring device in hospital, or health-care monitoring device at home, or the like. It may be seen that a plurality of electrodes 720 are located on the chest of the subject and the electrodes are configured for recording one or more potential changes of the subject. The potential changes may constitute an ECG waveform and the ECG waveform may be transmitted to the measurement module 710 by one or more wires. It also may be seen that one or more photoelectric sensors 730 are located on the finger of the subject and the photoelectric sensors are configured for detecting one or more PPG signals or pulse wave related signals. The detected signals may be transmitted to the measurement module 710 by wires or wirelessly. In this embodiment, the one or more photoelectric sensors are located on the finger of the subject and this arrangement or locating form is only provided for illustration purposes. In one example, the one or more photoelectric sensors may be located in the upper arm of the subject.

According to the embodiment, the calibration module 740 may include a cuff-based blood pressure monitor. The cuff-based blood pressure monitor may be configured for acquiring SBP and DBP values that may be used as calibration data (e.g., SBP0, DBP0, PTT0, or the like, or a combination thereof.) during one or more processes of the measurement module 710. As illustrated, the cuff-based blood pressure monitor may include a cuff, a pneumatic device (not shown in FIG. 7), a cable(not shown in FIG. 7), a transceiver (not shown in FIG. 7), and/or a controller (not shown in FIG. 7). The cuff may feature an internal, airtight pocket that may be secured onto a portion of a subject to deliver a pressure. For instance, the cuff may wrap around the subject's upper arm to deliver a pressure. The pneumatic device may include a pump, a valve, analog/digital converter, etc. During the process of acquiring calibration data, the pneumatic device may inflate the cuff and acquire a plurality of data (e.g., SBP0, DBP0, or the like, or a combination thereof.). The acquired data may be transmitted by the cable 750 to the transceiver (not shown in FIG. 7) for subsequent process.

The acquired ECG signal, PPG signal, calibration data (e.g., SBP0, DBP0, PTT0, or the like, or a combination thereof) may be transmitted to the measurement module 710 to be used for calculating a blood pressure value of the subject. The calculation may be performed by the measurement module 710, or may be performed by an analysis module (not shown) integrated in the measurement module 710. In some embodiments, the measurement module 710 may be a wearable or portable device separate from and capable of communicating with one or more photoelectric sensors 730, the electrodes 720, and/or the calibration module 740, as illustrated in FIG. 7. In some embodiments, the measurement module 710 may be packaged together with the calibration module 740. For instance, the measurement module 710 may be attached to the cuff of the calibration module 740.

Before the calculation, one or more operations may be performed, for example, pre-treatment, feature identification, feature estimation, calibration, or the like, or a combination thereof. More descriptions regarding the analysis may be found in International Patent Application No. PCT/CN2015/083334 filed Jul. 3, 2015 and International Patent Application No. PCT/CN/2015/096498 filed Dec. 5, 2015. The details may be displayed in the terminal 740, or may be transmitted to a related third party (for example, a medical institution). The details may be displayed in a display device (see FIG. 7) of the measurement module 710.

The monitoring device 700 may also include one or more additional components including a WIFI device, a blue tooth device, a NFC device, a GPS device, or the like, or a combination thereof. For instance, the WIFI device may be used for linking to a wireless network. The blue tooth device may be used for data transformation among some wired or wireless terminals within a certain distance. The NFC device may be used to enable terminals establishing radio communication within a short distance (10 cm or less). The GPS device may allow the subject to find his own position, or the GPS device may be used to navigate, or the like, or a combination thereof. The additional components may be connected or otherwise communicate with the measurement module 710, the calibration module 740, the terminal 740, and the server 120.

The monitoring device 700 may be used in a health care institute (e.g., a hospital), or may be used at home. The monitoring device 700 may be used for real time physiological feature monitoring. The acquired signals, information, data, or calculated physiological features of interest may be displayed in real time in a display device (not shown) or in the terminal 740. The subject, a user other than the subject (e.g., a doctor) may review the related information anywhere and anytime. In some embodiments, if the monitoring device 700 is used at home, the monitoring device 700 may communicate with a healthcare provider located in a location remote from the subject. The communication may be achieved directly by the monitoring device 700, or indirectly via, for example, the terminal 740 carried by the subject. The physiological feature, as well as location information, of the subject may be transmitted to the healthcare provider in real-time, periodically, or when a triggering event occurs. Exemplary trigger events are described elsewhere in the present disclosure. When an emergency occurs, for example, the physiological feature exceeding a threshold, the healthcare provider may be notified, the subject may be located based on the positioning information from the GPS or location sensor, and medical services may be provided accordingly.

Figure 8:
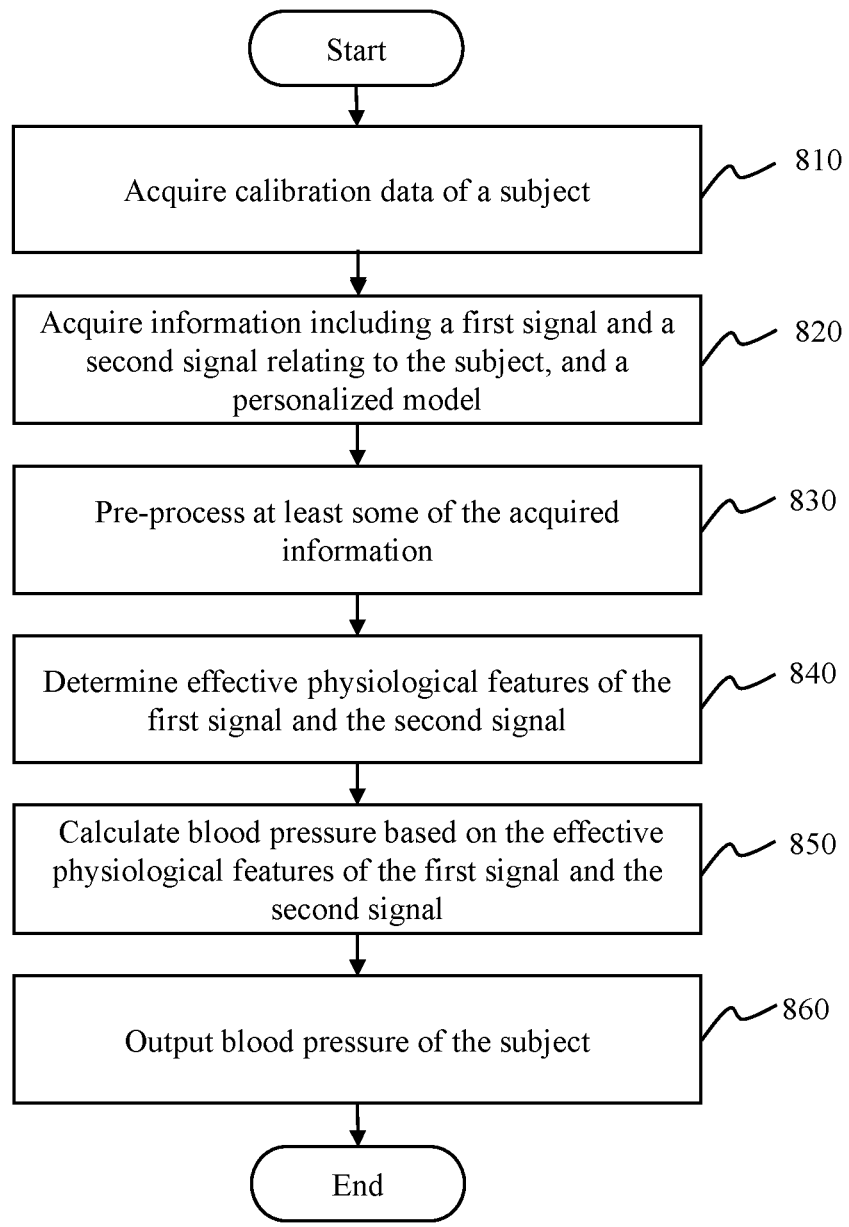
FIG. 8 provides exemplary processing regarding calculating blood pressure of a subject based on effective physiological features of the subject according to some embodiments of the present disclosure.

FIG. 8 is a flowchart diagram of an exemplary process for utilizing the disclosed method to estimate blood pressure according to some embodiments of the present disclosure. Beginning in step 810, calibration data of a subject may be obtained. The calibration data may be the ECG waveform and PPG waveform, together with the measured blood pressure (including SBP and DBP) using traditional Korotkoff sounds or an oscillometric method. Calibration data of the subject may be stored in the database 133. In some embodiments, the calibration may be taken while the subject is standing, sitting, or lying on a bed. The calibration may be taken at various time during the same or different daytime. For example, the calibration may be taken during the morning, noon, and/or night of a day.

In step 820, information including a first signal and a second signal relating to the subject may be acquired, together with a personalized model for the subject. The personalized model may be determined beforehand, choosing one of the models in the models 123 as in FIG. 1. The first signal may be an ECG signal. The second signal may be a PPG signal. In some embodiments, personal data regarding the subject may also be acquired in step 820.

In step 830, at least some of the acquired information may be pre-processed to dispose of the abnormal signal. For example, part of the PPG signals may be abnormal and need to be disposed of. In step 840, effective physiological features may be obtained using the first signal, second signal, and the personalized model for the subject. The effective physiological features may be used as model variables, and the personal data of the subject may be used as personal variable id for the personalized model.

In step 850, blood pressure based on the effective physiological features of the first signal and second signal may be calculated, using the designated personalized model and possibly personal data of the subject. The blood pressure of the subject may be output in step 860.

Figure 9:
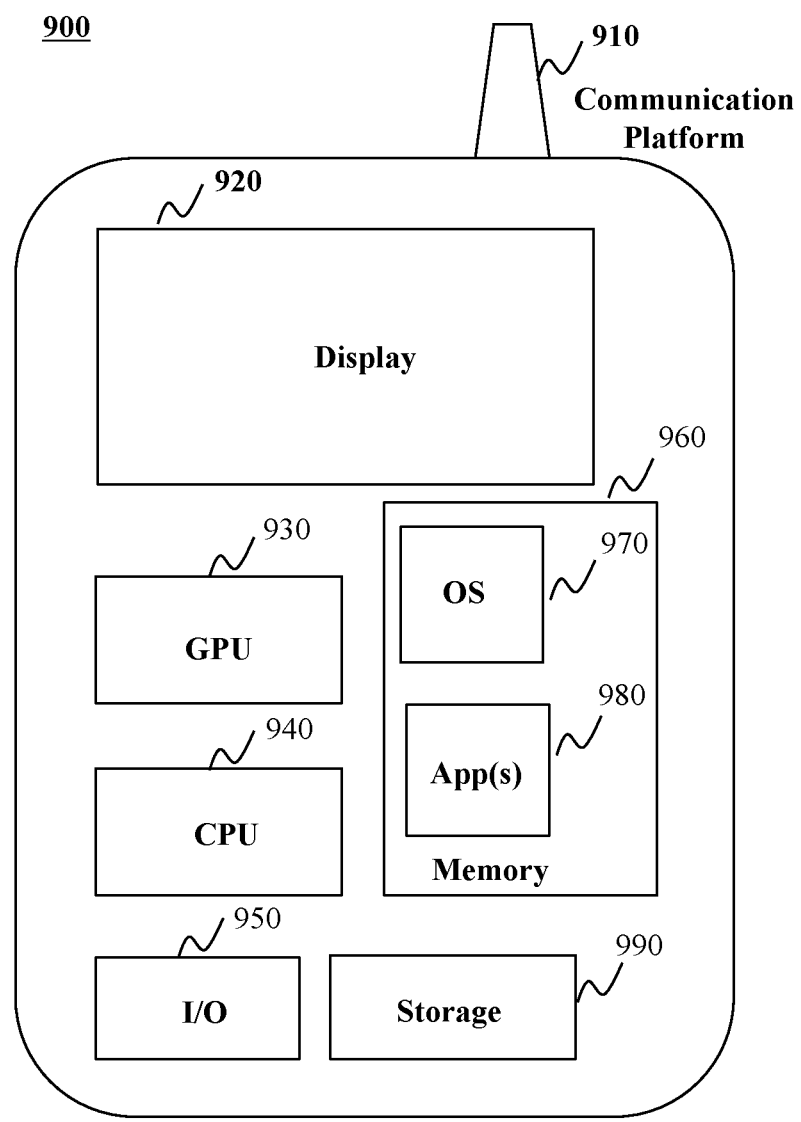
FIG. 9 depicts the architecture of a mobile device that may be used to implement a specialized system or a part thereof incorporating the present disclosure.

FIG. 9 depicts the architecture of a mobile device that may be used to realize a specialized system implementing the present disclosure. In this example, the device (for example, the terminal 140) on which information relating to blood pressure monitoring is presented and interacted-with is a mobile device 900, including, but is not limited to, a smart phone, a tablet, a music player, a handled gaming console, a global positioning system (GPS) receiver, and a wearable computing device (for example, eyeglasses, wrist watch, etc.), or in any other form factor. The mobile device 900 in this example includes one or more central processing units (CPUs) 940, one or more graphic processing units (GPUs) 930, a display 920, a memory 960, a communication platform 910, such as a wireless communication module, storage 990, and one or more input/output (I/O) devices 950. Any other suitable component, including a system bus or a controller (not shown), may also be included in the mobile device 900. As shown in FIG. 11, a mobile operating system 970, for example, iOS, Android, Windows Phone, etc., and one or more applications 980 may be loaded into the memory 960 from the storage 990 in order to be executed by the CPU 940. The applications 980 may include a browser or any other suitable mobile apps for receiving and rendering information relating to blood pressure monitoring or other information from the engine 200 on the mobile device 900. User interactions with the information stream may be achieved via the I/O devices 950 and provided to the engine 200 and/or other components of system 100, for example, via the network 150.

To implement various modules, units, and their functionalities described in the present disclosure, computer hardware platforms may be used as the hardware platform(s) for one or more of the elements described herein (for example, the engine 200, and/or other components of the system 100 described with respect to FIGS. 1-8). The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 10:
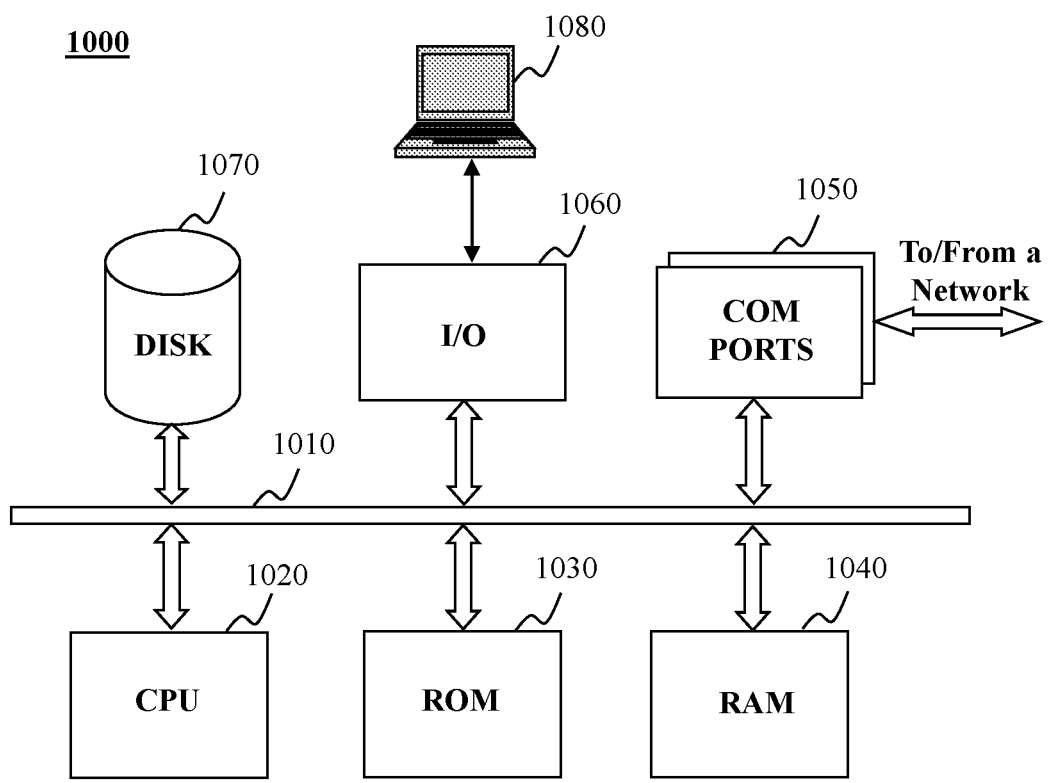
FIG. 10 depicts the architecture of a computer that may be used to implement a specialized system or a part thereof incorporating the present disclosure.

FIG. 10 depicts the architecture of a computing device that may be used to realize a specialized system implementing the present disclosure. Such a specialized system incorporating the present teaching has a functional block diagram illustration of a hardware platform that includes user interface elements. The computer may be a general purpose computer or a special purpose computer. Both may be used to implement a specialized system for the present disclosure. This computer 1000 may be used to implement any component of the blood pressure monitoring as described herein. For example, the engine 200, etc., may be implemented on a computer such as computer 1000, via its hardware, software program, firmware, or a combination thereof. Although only one such computer is shown, for convenience, the computer functions relating to the blood pressure monitoring as described herein may be implemented in a distributed fashion on a number of similar platforms, to distribute the processing load.

The computer 1000, for example, includes COM ports 1050 connected to and from a network connected thereto to facilitate data communications. The computer 1000 also includes a central processing unit (CPU) 1020, in the form of one or more processors, for executing program instructions. The exemplary computer platform includes an internal communication bus 1010, program storage and data storage of different forms, for example, disk 1070, read only memory (ROM) 1030, or random access memory (RAM) 1040, for various data files to be processed and/or transmitted by the computer, as well as possibly program instructions to be executed by the CPU. The computer 1000 also includes an I/O component 1060, supporting input/output between the computer and other components therein such as user interface elements 1080. The computer 1000 may also receive programming and data via network communications.

Hence, aspects of the methods of the blood pressure monitoring and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of the engine 200 into the hardware platform(s) of a computing environment or other system implementing a computing environment or similar functionalities in connection with the blood pressure monitoring. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present disclosure are amenable to a variety of modifications and/or enhancements. For example, although the implementation of various components described above may be embodied in a hardware device, it may also be implemented as a software only solution—for example, an installation on an existing server. In addition, the blood pressure monitoring system as disclosed herein may be implemented as a firmware, firmware/software combination, firmware/hardware combination, or a hardware/firmware/software combination.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure. In addition, the term "logic" is representative of hardware, firmware, software (or any combination thereof) to perform one or more functions. For instance, examples of "hardware" include, but are not limited to, an integrated circuit, a finite state machine, or even combinatorial logic. The integrated circuit may take the form of a processor such as a microprocessor, an application specific integrated circuit, a digital signal processor, a micro-controller, or the like.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "unit," "module," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—for example, an installation on an existing server or mobile device. In addition, the financial management system disclosed herein may be implemented as a firmware, firmware/software combination, firmware/hardware combination, or a hardware/firmware/software combination.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. A device for monitoring blood pressure comprising:
   memory storing instructions; and
   at least one processor that executes the instructions to perform operations comprising:
   receiving a plurality of second signals representing time-varying information on a pulse wave of a subject;
   determining a plurality of effective physiological features of the subject based on the plurality of second signals;
   designating a personalized model for the subject from a plurality of models based on cost function of each of the plurality of models and the plurality of effective physiological features; and
   calculating a blood pressure of the subject based on the effective physiological features and the designated personalized model for the subject.

2. The device of claim 1, wherein the cost function is a standard deviation of prediction errors of test data, the test data being the plurality of effective physiological features with the minimal cross-validated prediction errors.

3. The device of claim 2, wherein the designated model for the subject is a model with a minimum standard deviation of the prediction errors of the test data.

4. The device of claim 1, wherein the plurality of effective physiological features of the subject are determined based on Akaike information criterion (AIC).

5. The device of claim 1, wherein the plurality of second signals comprise a PPG waveform.

6. The device of claim 1, further being configured to receive a first signal representing the pulse wave relating to heart activity of the subject, wherein the first signal is used to determine the plurality of effective physiological features of the subject.

7. The device of claim 6, the first signal comprises an ECG waveform or a BCG waveform.

8. The device of claim 1, further being configured to communicate with a cuff-based blood pressure monitor.

9. The device of claim 8, wherein the cuff-based blood pressure monitor is configured to coordinate a blood pressure measurement with the receiving of the plurality of second signals.

10. A method implemented on a computing device having at least one processor and a non-transitory storage medium for monitoring blood pressure, the method comprising:
receiving a plurality of second signals representing time-varying information on a pulse wave of a subject;
determining a plurality of effective physiological features of the subject based on the plurality of second signals;
designating a personalized model for the subject from a plurality of models based on cost function of each of the plurality of models and the plurality of effective physiological features; and
calculating a blood pressure of the subject based on the effective physiological features and the designated personalized model for the subject.

11. The method of claim 10, wherein the cost function is a standard deviation of prediction errors of test data, the test data being the plurality of effective physiological features with the minimal cross-validated prediction errors.

12. The method of claim 11, wherein the designated model for the subject is a model with a minimum standard deviation of the prediction errors of the test data.

13. The method of claim 10, wherein the plurality of effective physiological features of the subject are determined based on Akaike information criterion (AIC).

14. The method of claim 10, wherein the plurality of second signals comprise a PPG waveform.

15. The method of claim 10, further comprising receiving a first signal representing the pulse wave relating to heart activity of the subject, wherein the first signal is used to determine the plurality of effective physiological features of the subject.

16. The method of claim 15, the first signal comprises an ECG waveform or a BCG waveform.

17. The method of claim 10, further comprising communicating with a cuff-based blood pressure monitor.

18. A system for monitoring blood pressure, comprising
at least one processor;
a non-transitory storage medium;
a acquisition module configured to receive a plurality of signals representing time-varying information on the pulse wave;
an analysis module configured to receive a plurality of second signals representing time-varying information on a pulse wave of a subject;
determine a plurality of effective physiological features of the subject based on the plurality of second signals;
designate a personalized model for the subject from a plurality of models based on cost function of each of the plurality of models and the plurality of effective physiological features; and
calculate a blood pressure of the subject based on the effective physiological features and the designated personalized model for the subject.

* * * * *